United States Patent [19]
Langford

[11] Patent Number: 5,443,801
[45] Date of Patent: Aug. 22, 1995

[54] ENDOSCOPE CLEANER/STERILIZER

[75] Inventor: Terrence R. Langford, Tucson, Ariz.

[73] Assignee: KEW Import/Export Inc., Tucson, Ariz.

[21] Appl. No.: 62,958

[22] Filed: May 14, 1993

Related U.S. Application Data

[63] Continuation-in-part of Ser. No. 954,979, Sep. 30, 1992, Pat. No. 5,245,845, which is a continuation-in-part of Ser. No. 774,047, Oct. 8, 1991, Pat. No. 5,184,633, which is a continuation-in-part of Ser. No. 556,570, Jul. 20, 1990, abandoned.

[51] Int. Cl.⁶ .............................................. A61L 2/00
[52] U.S. Cl. .................................. 422/294; 134/137; 134/147; 134/161; 422/186.07; 422/296; 422/297
[58] Field of Search ...................... 422/28, 29, 33, 108, 422/294, 296, 297, 305, 186.07, 186.08, 186.14, 186.20, 119, 112, 102, 104, 292; 134/137, 147, 161; 366/208, 333; 383/43

[56] References Cited

U.S. PATENT DOCUMENTS

| | | | |
|---|---|---|---|
| 2,499,162 | 2/1950 | Rand | 366/208 |
| 3,910,761 | 10/1975 | Hopkins | 422/108 |
| 4,010,786 | 3/1977 | Aguettant et al. | 383/202 |
| 4,194,622 | 3/1980 | Lewis | 422/119 |
| 4,667,691 | 5/1987 | Sasa | 134/169 C |
| 4,785,940 | 11/1988 | Wilson | 383/211 |
| 4,903,718 | 2/1990 | Sullivan | 134/184 |
| 4,923,681 | 5/1990 | Cox et al. | 422/119 |
| 5,034,198 | 7/1991 | Kaiga et al. | 422/186.07 |

FOREIGN PATENT DOCUMENTS

| | | | |
|---|---|---|---|
| 0072257 | 2/1983 | European Pat. Off. | 422/292 |
| 2094150 | 9/1982 | United Kingdom | 422/292 |
| 2199496 | 7/1988 | United Kingdom | 422/292 |
| 0000590 | 8/1978 | WIPO | 383/211 |

Primary Examiner—James C. Housel
Assistant Examiner—Laura E. Collins
Attorney, Agent, or Firm—Ogram & Teplitz

[57] ABSTRACT

A cleansing/sterilizing apparatus which is a transportable apparatus and method for inside-outside and sterilization of various complex reusable medical/dental instruments, including but not limited to laparoscopic instruments and dental handpieces. The apparatus avoids the use of heat, pressure, severe agitation, or corrosive chemicals which might damage delicate equipment. The apparatus preserves each processed instrument hermetically sealed in a sterile dry environment within a detachable/portable capsule until its next use.

29 Claims, 11 Drawing Sheets

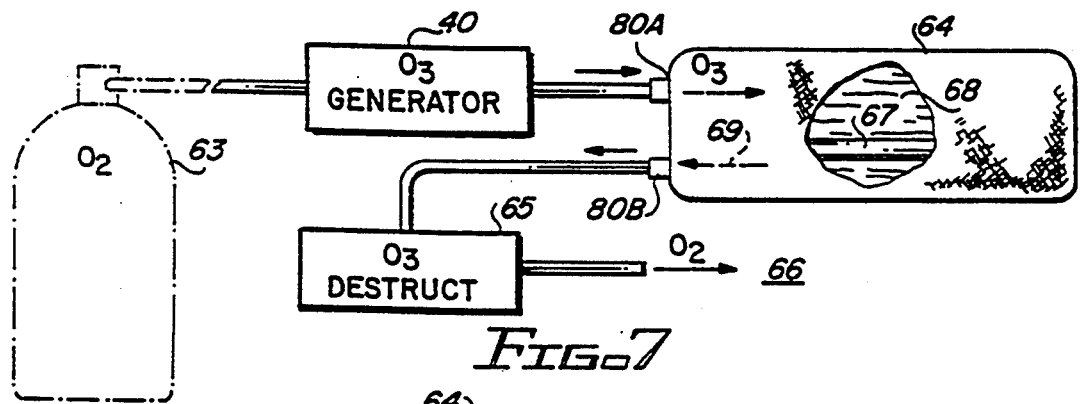
FIG. 7
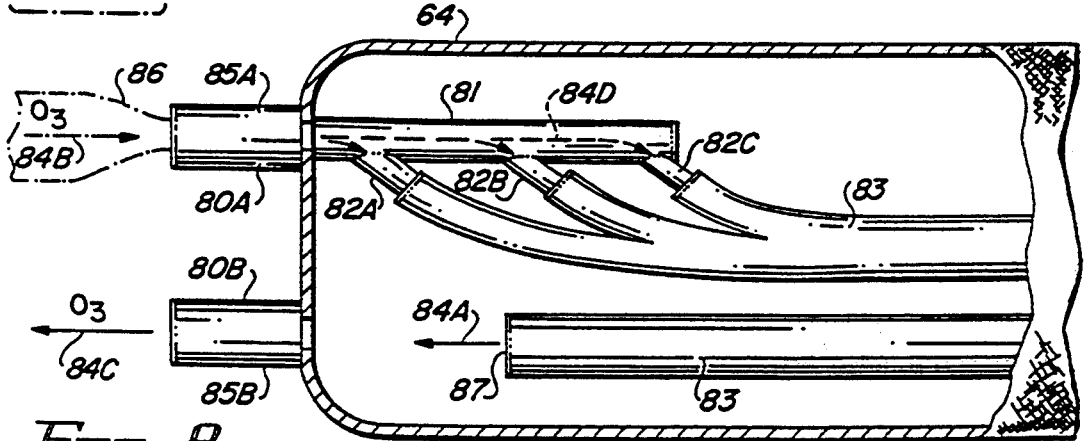
FIG. 8
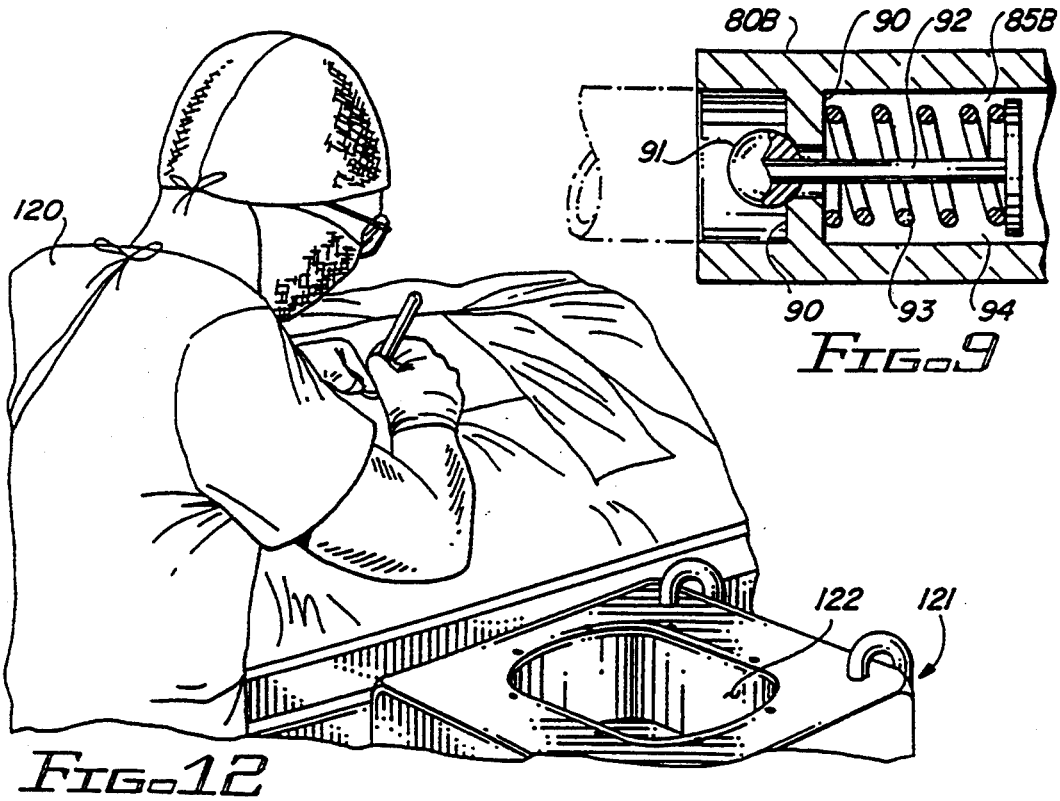
FIG. 9
FIG. 12

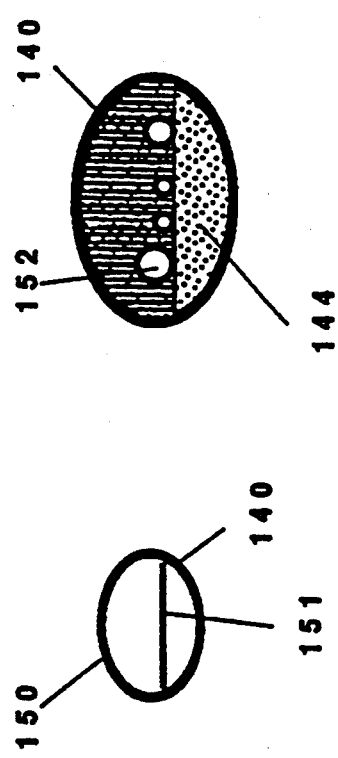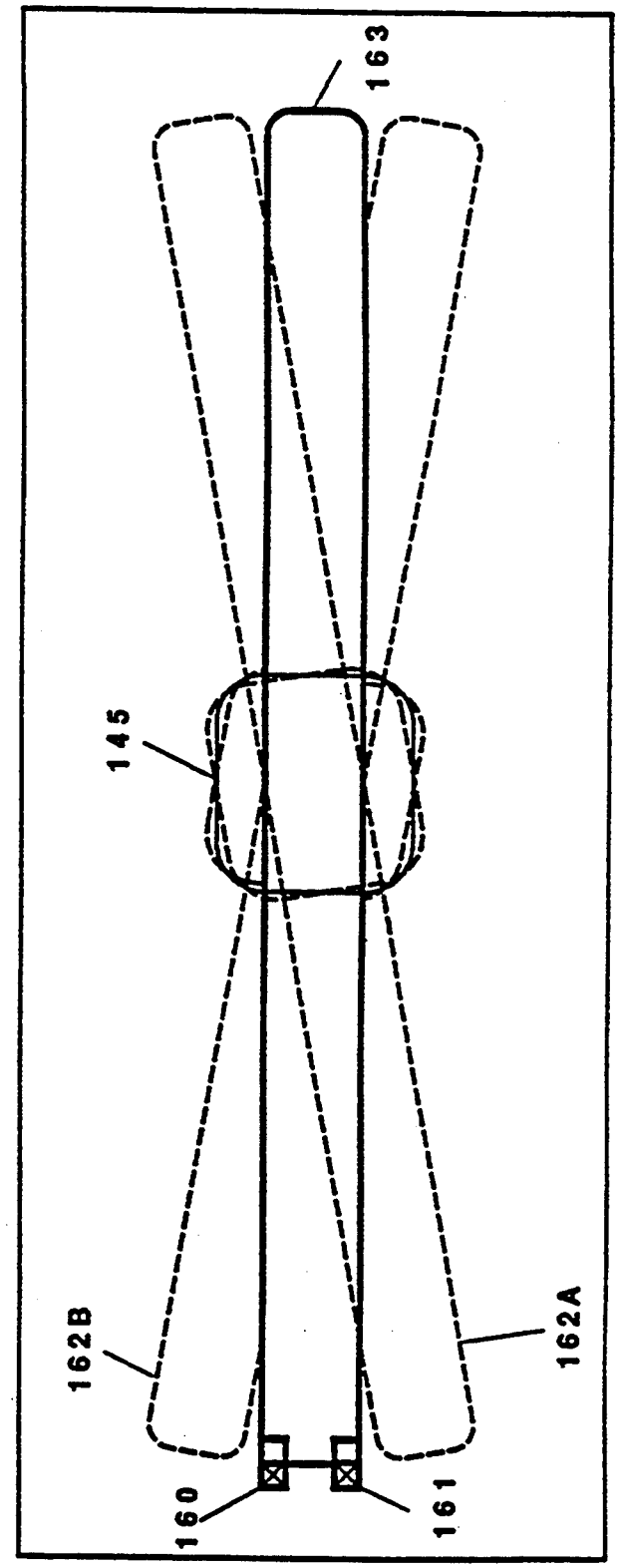
Fig 15A Fig 15B
Fig 16

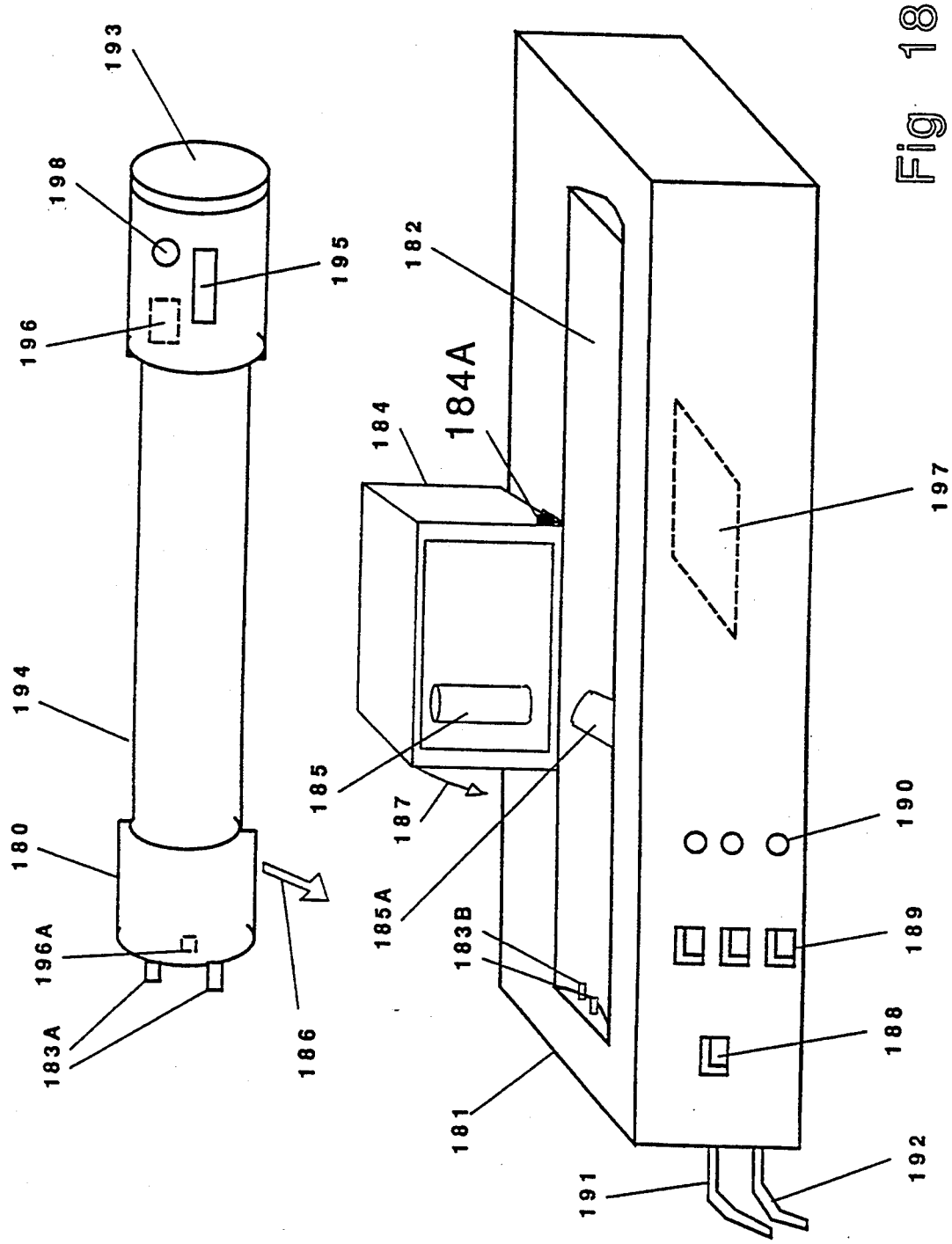

ENDOSCOPE CLEANER/STERILIZER

This is a continuation-in-part of U.S. patent application Ser. No. 07/954,979, entitled "Flexible Article Sterilizing Mechanism" filed Sep. 30, 1992, now U.S. Pat. No. 5,245,845, which was a continuation-in-part of U.S. patent application Ser. No. 07/774,047, entitled "A Cleansing and Sterilization Mechanism Suitable for Contact Lenses and the Like" filed Oct. 8, 1991, now U.S. Pat. No. 5,184,63 ; which was a continuation-in-part of U.S. patent application Ser. No. 07/556,570, entitled "A Contact Lense Device and Method" filed Jul. 20, 1990, now abandoned.

BACKGROUND OF THE INVENTION

This invention relates generally to sterilizing systems and particularly to sterilizing systems which utilize ozone suspended in a liquid as the sterilizing agent and more particularly to sterilizing systems for endoscopes.

This invention is particularly adapted to endoscope cleaning and sterilization.

Although this invention has tremendous applications to a variety of items to be cleaned including but not limited to, dental tools, surgical instruments, implants, etc., for an understanding of the problems associated with cleansing and sterilization, the following discussion focusses on the cleansing and sterilization of contact lenses.

The success or tragic failure of contact lens wear is ultimately determined by the care and aseptic handling of the lenses. With over seventeen million contact lens wearers in the United States spending two billion dollars on contact lens supplies, a simple one step cleaning and sterilizing process is sought. Both hard and soft lenses currently need daily, or in the case of extended wear contacts, weekly cleaning and antiseptic treatment.

By their very nature, being in close relationship with the wearer for extended periods of time, contact lenses are susceptible to both: buildups of protein and lipids from the wearer; and also from contamination from microorganisms. Either of these, buildup or contamination, can have debilitating affects such as reduced vision, scarring of the eye, and even blindness.

Hydrophilic contact lenses, being soft and composed mainly of water, have made the problem of cleaning even more difficult. Physical pressure on the hydrophilic lense may cause rips; strong disinfectants become lodged within the body of hydrophilic lense itself and then irritate the wearer's eye causing an ulcer.

Without a good cleaning process, both the hard and soft contact lense is susceptible to a wide variety of contaminating microorganisms including:

Acanthamoeba, Pseudomonas organisms, Alcaligenes faecalis, staph, Aureus, and Enterobacter aerogenes.

For a through understanding of the diseases associated with contact lenses, see: "Pseudomonas aeruginosa Contamination of Hydrophilic Contact Lenses and Solutions", by Milauskas, appearing in *Transactions of the American Academy of Ophthalmology and Otology*, vol. 76, March–April 1972, page 511; "Complications Associated with Contact Lens Solutions", by Morgan, appearing in *Ophthalmology AAO*, vol. 86, June 1979, page 1107; "The Soft Plastic Contact Lenses" by Dastoor, appearing the *Indian Journal of Ophthalmology*, vol. XXI, on page 25; "Microbiological Evaluation of Soft Contact Lens Disinfecting Solutions" by Houlsby et al., appearing in the *Journal of the American Optometric Association*, vol. 55, Number 3, page 205; and, "Susceptibility of Acanthamoeba to Soft Contact Lense Disinfection Systems", appearing in the *Investigative Ophthalmology & Visual Science*, April 1986, Vol. 27, page 626.

Additionally, the high water content of hydrophilic contact lenses make them more susceptible to the formation of "jelly bump" deposits which are composed primarily of lipids and calcium. These lipid formations are usually long and intermediate chain cholesterol esters and triglycerides which are particularly difficult to remove from a soft lense without damaging the lense. A good review of this problem is "Origin and Composition of Lipid Deposits on Soft Contact Lenses" by Hart et al., and appearing in *Ophthalmology*, April 1986, vol. 93, No. 4, page 495.

The typical method of cleaning, using a saline solution and distilled water approach has not been totally satisfactory. It has been found that this approach does not truly address the contamination problem; indeed, several of the contaminating microorganisms actually thrive in the cleaning environments.

Because of this, the industry has been seeking alternative cleaning approaches which may be used by the wearer, not a laboratory.

One technique proposed is the use of a 3% hydrogen peroxide solution for the cleaning and disinfecting the lenses. The reason for this popularity is that after disinfecting, the hydrogen peroxide is converted into innocuous by-products which are compatible with ocular physiology.

The hydrogen peroxide approach is well described in: "A Comparison of New Hydrogen Peroxide Disinfection Systems" by Krezanoski et al., and appearing in the *Journal of the American Optometric Association*, vol, 59, No. 3, page 193; "Efficacy of Hydrogen Peroxide Disinfection Systems for soft Contact Lenses Contaminated with Fungi", by Penley et al., and appearing in the *CLAO Journal*, Jan. 1985, vol. 11, no. 1, page 65; "Reaction to Hydrogen Peroxide in a Contact-Lens Wearer", by Knopf, appearing the *American Journal of Ophthalmology*, June, 1984, page 796; "Hydrogen Peroxide in Anterior Segment [Physiology: A Literature Review", by Chalmers, appearing in *Optometry & Vision Science*, page 796; and, "Hydrogen Peroxide Sterilization of Hydrophilic Contact Lenses", by Gasset et al., and appearing in *Arch. Ophthalmology*, vol, 93, June 1975, page 412.

Unfortunately, hydrogen peroxide, at the 3% level or even the 6% level, is incapable of disinfecting some of the hardier microorganisms. Further, hydrogen peroxide does not have noticeable affect upon the "jelly bumps".

Perhaps the most common treatment is the heat method. In this approach the contact lenses are exposed to a temperature of eighty degrees centigrade for a period ten minutes. This approach is more effective than chemicals against microorganisms but the treatment substantially decreases the life of the contact lenses and is usable only with about half of the present contact lenses. Use of this method depends heavily upon the water content and the type of plastic used in the lenses' construction.

Additionally, proteins and other contaminants that are left in the contact lense (buildup) can substantially produce irritation in the eyes of the user.

Although the problems associated with contact lenses are immense, they pale in comparison to the hurdles encountered in cleaning and/or sterilizing endoscopes. Endoscopes are flexible tubes having a multiplicity of endings. Merely soaking endoscopes in a sterilant or detergent is unacceptable since numerous pockets existing within the tubing where the sterilant or detergent cannot effectively reach.

Once used, endoscopes are usually discarded due to the complexity in getting the endoscope sterilized before any subsequent uses. Endoscopes themselves are extremely expensive so their disposal after one use is seen as wasteful since the structural integrity of the endoscope has not been jeopardized by its use, only its sterile nature.

It is clear from the foregoing that an efficient and through cleaning and sterilizing technique does not exist.

SUMMARY OF THE INVENTION

Within the present invention, the apparatus is transportable and permits inside-outside washing and sterilization of various complex reusable medical/dental instruments and endoscopes, including but not limited to laparoscopic instruments and dental handpiece. The apparatus avoids the use of heat, pressure, severe agitation, or corrosive chemicals which might damage delicate equipment. The apparatus preserves each processed instrument hermetically sealed in a sterile dry environment within a detachable/portable capsule until its next use.

The apparatus functions in four sequential cycles: wash, rinse, sterilize, and dry. All cycles and safety features are controlled automatically by means of a computer system having microprocessor program firmware and electromechanical sensors and actuators. Status messages to the operator are generated in the microprocessor and delivered through Liquid Crystal Display (LCD) alphanumeric displays and Light Emitting Diode (LED) indicator lamps.

In the preferred embodiment, the apparatus uses water that has been pruified by means of filters or distillation. Those of ordinary skill in the art readily recognize a variety of methods which can be used to create purified water.

The apparatus washes by means of detergent dissolved in purified water, rinses by means of purified water, sterilizes by means of ozonated and purified water, and dries by means of ozonated/deozonated sterile warm dry oxygen, or sterile inert gas.

Agitation within the apparatus is by means of a peristaltic pump. The pumping function is accomplished by means of a pre-sterilized, compressible, disposable diaphragm that the operator places within the capsule somewhere between the open ends of the laparoscopic instruments on the rack. The action of the pump and the diaphragm forces oscillating surges of cleansing/sterilizing agent through the insides and over the outside of the laparoscopic instruments contained in the wash chamber.

Upon completion of the drying cycle, the wash chamber in the apparatus remains under a slight positive pressure above atmospheric. This pressure causes the peristaltic segment in the wall of the chamber to bulge slightly. This bulge provides a visual verification of the integrity of the chamber seal, and the sterility of the contents, until the chamber is opened.

There is no cross-contamination between successive loads because one-way valves assure the integrity of inlet/outlet flows, and ozonation assures sterility of those valves and of the wash chamber.

In the preferred embodiment, the hermetically sealed capsule in the apparatus is oval in cross section to accommodate a wider rack inside a smaller volume. Instruments are introduced into the capsule through a hermetic access port in one end. Liquids and gases are injected into the capsule and exhausted or drained from the capsule through a set of four one-way valves with detachable couplings at the other end.

The device accommodates the longest endoscopic instruments laid out full length by means of a U-shaped version of the hermetically sealed capsule. The one-way valves are in the end of the inner arm of the "U". The pump and diaphragm are in the middle of the inner arm of the "U". A double-wide hermetic access port is in the base of the "U". The ends of the longer laparoscopic instruments extend into the outer arm of the "U". The loaded instrument rack, fitting the shape of the "U", is introduced ends first into the double-wide capsule.

For the preferred embodiment, the device requires the following utility connections: water source, ordinary sewer, AC power, oxygen gas, and an ordinary vent to outside air. Since a detachable modular capsule on the apparatus encloses each endoscopic instrument, a surgical facility has the option to sterilize either on-site in a single Operating Room (O.R.) or in a centralized location, with sealed capsules being conveyed safely into and out of a number of Operating Rooms as needed.

The detergent used in the apparatus wash cycle has a high pH and is therefore anti-corrosive to metallic parts in the laparoscopic instruments. Its high solubility assures a residue-free rinse.

A measured amount of detergent is assured for each wash by means of a detergent capsule dispenser in the apparatus, which contains safety sensors and electronic logic that prevents initialization of the washer cycle when a fresh capsule is not in place.

The effectiveness of the apparatus' function is not dependent upon the quality of an external prewash or soak cycle because the apparatus is capable of washing and flushing any large lipid particulates that may be clinging to the inside or outside of endoscopic instruments.

In operation of the preferred embodiment, the operator:

(1) opens the peristaltic pump housing;
(2) selects an empty capsule of oval cross section;
(3) mounts it horizontally so that fittings on the tilt mechanism mate with the capsule's fittings;
(4) closes and latches the peristaltic pump housing;
(5) connects the two water ports (inlet and drain) and the two gas ports (inlet and vent) on one end of the Capsule to mating connectors on hoses hanging outside the device;
(6) opens the access port door on the other end of the capsule and pulls out the Instrument Rack;
(7) lays out the endoscopic instrument lengthwise on the rack;
(8) adjusts the endoscopic instrument longitudinally to avoid placing any bulky parts in the peristaltic segment of the wash chamber;
(9) installs a compressible, disposable diaphragm on the rack in a location nearest to an approximate midpoint between all the openings in the endoscopic instrument;

(10) inserts the loaded rack with the diaphragm through the open hermetic access port onto a track within the wash chamber of oval cross section

(11) secures the rack by means of a latch on the track;

(12) closes and seals the access port door;

(13) inserts a fresh detergent capsule into the detergent Dispenser;

(14) selects a Wash/Rinse/Sterilize Cycle; and,

(15) presses the "Cycle Start" button.

From this point on, the operation is automatic. There are three alternative Wash/Rinse/Sterilize cycles which are distinguished by the sequence in which the oxidant/steriliant Ozone, $O_3$, is introduced into the system. The sterile gas used in each "drain" operation may be either $O_2$, $O_3$, or an Inert gas.

Drying of the contents within the capsule is also done automatically. This involves operating the peristaltic pump while dry sterile gas is being injected into and exhausted from the Wash Chamber; maintaining a positive pressure relative to atmospheric, to assure sterility of the contents; and tilting the Wash Chamber Capsule back to horizontal.

To dismount the capsule, the operator disconnects the two water ports (inlet and drain) and the two gas ports (inlet and vent) on one end of the capsule from mating connectors on hoses hanging outside the apparatus device. The operator opens the peristaltic pump housing, lifts off the loaded and hermetically sealed capsule, and places it in a storage location pending the next use of its contents.

To unload the capsule, the operator opens the access port door on the access end of the capsule, unlatches the instrument rack, and pulls it out. The operator removes the diaphragm and disposes of it as "green drapes" (clean) waste. The endoscopic instruments are sterile to the moment of opening the hermetic access port in the capsule, and they are ready for surgical use.

Other embodiments of the invention permit a wider range of cleansing and sterilizing.

In the present invention, a liquid bath, preferably of distilled water, is kept in a pressure vessel and gaseous ozone is diffused into the liquid. The ozonenated liquid is then used as a steriliant in a container which is engagable with the pressure vessel. In the preferred embodiment the container and the pressure vessel are chilled to maintain the ozone diffused in the liquid. Excess liquid from the container is communicated to a destruct mechanism such as activated charcoal or discharged into the waste water system.

The invention has applications to a variety of embodiments which are discussed herein.

In the preferred embodiment of the invention, a cleansing and sterilization mechanism is created which is usable on contact lenses, surgical instruments, dental tools, and other items which require regular cleansing and sterilization. Using ozone as the cleansing and sterilization medium, the apparatus provides for added guaranty of operation through the use of feedback mechanism to assure that all the components are working and that the to-be-cleaned items are exposed to the ozone bath for the specified time. Furthermore, the item is capable of communicating, vis phone line, to a central unit which monitors the operation and performance of the mechanism.

Fundamentally the present invention consists of a housing having therein an ozone generator, a pump, and a controller. A container holding the items to be sterilized and cleansed is insertable into the housing. The controller assures that both the pump and ozone generator are operating. Via valves in the container, ozone is directed over the to-be-cleaned items forming an ozone bath. After the proper amount of time has elapsed, the controller either shuts down the pump and ozone generator, or the controller redirects the ozone to another container (depending on the embodiment in use).

The container, With the now sterilized items, is removable from the housing and may be carried with the user or moved to a location where the items will be used (i.e. in an operating theater, moved to the operating table). The items within the container are kept sterile through the use of self-sealing valves which seal when the container is removed from the housing.

Although the present invention relates to a variety of items, the application of cleansing of,contact lenses is one of the major applications. Because of this, the following discussion relates to the present invention's application to this field.

An ozone generator creates a bath of ozone and saline. A cage or other suitable arrangement, submerges the contact lenses into this bath for a predetermined amount of time. A timer either deactivates the ozone generator at the proper time or alerts the user so that the contact lense should be removed from the bath.

Ozone was discovered in 1840 by Christian Friedrich Schonbein. Ozone is three oxygen atoms bonded together. Unfortunately, ozone has a very short life, usually about twenty minutes. As the ozone breaks down, its natural by products are pure water and stable oxygen.

It is the off-gas ozone which has created the largest concern for health reasons. Standards for the protection of users range in the 0.10 to 0.12 parts per million range.

Because of ozone's ability to control bacteria and virus microorganisms, ozone has been used since the 1890's to purify water for drinking. More recently, ozone has been used in swimming pools to reduce the dependency on chemical purification.

Production of ozone is typically created by passing air past an ultraviolet light in a sealed chamber. This produces an ozone-rich air which is then pumped into a saline bath.

Sterilization using ozone is effective for all ocular pathogens including viruses, bacteria, fungus, and most importantly amoebae. The time of actual ozone exposure to the contact lenses is less than or equal to the present method of heat or chemical aseptisizing, usually ten minutes.

Ozone is the second most powerful oxidant known. This means that ozone: is a powerful oxidant for pollutants and organic contaminants; and, is an excellent steriliant for microorganisms. When compared to chorine, ozone has an oxidizing potential 50% greater and can destroy bacteria and viruses up to three thousand times faster.

Ozone is also a strong oxidizing agent which causes small suspended particles to coagulate and precipitate away from the contact lenses. This assists in the cleaning of the contact lenses since removed matter is quickly and effectively removed from the proximity of the contact lense.

Two different levels of the present invention are envisioned: the first is a home-use apparatus for the cleaning of a single pair of contact lenses; the second is an eye care practitioner's office apparatus for the production cleaning of multiple contact lenses.

The invention is particularly powerful for the home use application. In this situation, the main part which fails in the cleansing and contact lenses is the user himself. Typically, the user forgets to cleanse the contact lense and then "swears" to his doctor that the cleansing was done religiously.

In certain countries, especially European countries, the responsibility of assuring that the user does clean the contact lenses falls upon the physician. Because of this, the physician wants to be sure that i) the user is using the device, and ii) the user will return to the physician regularly for follow-up examinations.

In the preferred embodiment, the present invention accomplishes these objectives by having a prescribed number of "cleanings/sterilizations" logged onto a memory chip. The user is able to use the device only this many times and then must return to the physician to have the use data reestablished. Furthermore, the physician is able to poll the device, via the phone lines, as to the actual number of uses the user has made of the device.

In operation, the preferred embodiment of the invention:

1) The power is turned on to the unit by the user;
2) The on-board computers checks to see if the pump and ozone generator lamp are off;
3) The computer checks to see how many counts are remaining in the memory count-down;
4) Based upon these checks, the computer,
   a) If the count is zero, the computer notifies the via such devices as flashing Light Emitting Diodes (LEDs) and shuts down the operation, or,
   b) If the count is under a predetermined warning level (i.e. 10), then the operator is notified via the LEDs and the ozone generator and pump are activated, or,
   c) If the count is above the warning level, the computer notifies the user via the LEDs and the ozone generator and pump are activated;
5) The computer waits a short period of time (i.e. 300 milliseconds) and checks to see that the pump and light are activated;
6) The computer waits another short period of time (i.e. 1 second) and checks to see if gas flow is detected [note- steps 5 and 6 are safety checks to see if the apparatus is working];
7) After the prescribed amount of time (i.e. 19 minutes) the computer shuts off the ozone generator permitting the pump to continue operation to purge the system; and,
8) After the ozone generator is deactivated, the pump operates a short period (i.e. 1 minute) before the computer deactivates the pump.

Studies conducted have found that using an ozone generator producing 0.02 grams of ozone per hour requires a submersion of 3 minutes for a thorough cleaning.

In an enhanced embodiment, the contact lenses are automatically removed from the ozone bath at the termination of the proper elapsed time and the ozone generator is switched "off". Once removed from the ozone bath, the contact lenses are rinsed with a saline solution, permitting any ozone which may have impregnated the lenses, particularly hydrophilic contact lenses, to break down into harmless elements.

The preferred embodiment of the present invention utilizes an ozone generator producing from 0.01 grams to 1 gram of ozone per hour. This is the preferred level since it reduces any health dangers which might occur form air-suspended off-gassed ozone. Those of ordinary skill in the art readily recognize how to construct an ozone generator having this capability.

Those of ordinary skill in the art acknowledge the use of two procedures to produce ozone: ultraviolet radiation; and, corona discharge.

Most ozone generators currently use-ultraviolet radiation. These are usually the lowest cost ozone generators on a per unit basis. This decrease in cost is due to the fact that the air does not go through an initial drying process.

Newer units being produced utilize a corona discharge technique which dry the air before charging the air with ozone. This drying permits the corona discharge apparatus to produce a higher ozone concentration.

For minimal expenditures of electrical energy, ozone normally is produced from dried air ($-60$ degrees fahrenheit dew point) in concentrations of one to two percent and from dry oxygen in concentrations of two to four percent. More than eighty percent of the electrical energy applied to the electric discharge field is converted to heat and, if this is not quickly removed from the cell, the heat causes rapid decomposition of the ozone back to oxygen. The rate of this reverse reaction increases rapidly above thirty-five degrees centigrade. Proper cooling of the ozone generator cells is critical to maintaining consistent yields of ozone.

For the second type of apparatus, that of a production cleaning device in an eye care practitioner's office, multiple containers are used for cleaning several sets of contact lenses simultaneously (or alternatively for cleaning several sets of surgical instruments or dental tools). In this application the controller also detects when a container is placed with a slot in the housing and then operates on the multiple containers on a first come-first served approach.

If the ozone generator is sufficiently large, then multiple containers may be cleansed/sterilized simultaneously.

For both versions, the air flow is generated by a bellows type low pressure pump. Those of ordinary skill in the art readily recognize other pumps which will serve this function.

Also, for all the applications, the containers are automatically sealed upon removal from the housing. This is accomplished by any of several mechanisms well known to those in the art.

This feature, of sealing upon removal, permits the transportation of the contact lense, or other such device, without fear of contamination. In the preferred embodiment, when the lid to the container is opened, this opening shifts and indicia so that, later, the user is able to determined that the container has been opened and that the items are no longer considered sterile.

In the production cleaning embodiment, the ozone generator preferably produces 0.01 grams to 5 grams of ozone per hour.

Studies have determined that ozone levels of as low as 0.001 grams per hour are effective and that 0.006 grams per hour is an efficient balance between sterilizing affect and energy demands for the generation of the ozone.

One important attribute of the present invention is its ability to provide a variety of levels of "cleaning". It has been found that by varying the amount of ozone and the amount of elapsed time of exposure, contact lenses may be disinfected, asepticized, or even sterilized. None of the current state of the art devices can achieve these results without damaging the contact lenses or producing harmful effects to the eye.

A plethora of related inventions are also involved with the core preferred embodiment. These inventions expand upon the capability and functionality of the preferred invention.

In a variety of situations, the need exists for a "dry" ozone stream. Many instruments and devices either rust or corrode if exposed to a humid or wet environment. To this end, a recognition of Henry's Law where at sufficiently high dilution in a liquid solution, the fugacity of a nondissociating solute becomes proportional to its concentration is important; hence, through the proper manipulation of temperature and pressure, the life of ozone, whether in a liquid such as water or in a gaseous steam, is prolonged.

In the preferred embodiment of a dry ozone stream, a pressurized source of oxygen communicates with the ozone generator. This pressurized oxygen is "dry" in that no water vapor is present. The ozone generator creates ozone from some of the oxygen and communicates an ozone/oxygen gaseous stream. The stream is ideal for treatment of surgical instruments (dental and medical instruments) which would degrade if water was present.

One particularly useful aspect of the present invention is an adapter which is used to communicate the ozone from the ozone generator into a hollow tubing. Within the medical industry, a variety of tubes are used for such applications a gastroscopy, colonoscopy, or other such endoscopy examinations. These tubes are generally hollow with two or more openings into which tools for physician viewing or treatment is inserted and communicated to the area of concern. Once used, these tools are contaminated and must be either sterilized or discarded. Sterilization of these tubes is particularly difficult since the tubes are destroyed with intense heat (eliminating the autoclave as a sterilizing mechanism) and chemical treatment does not always probe into every crevice within the tube, leaving contaminated pockets within the tubing.

In the present invention, an adapter is used to directly communicate ozone from the inlet of the container to all but one of the openings in the tube.

As example, assume there are N (N being an integer greater than one) openings in the tube. The adapter communicates with all of the openings except for one of them. Ozone therefore is passed into the tube in such a manner that it must flow through all areas of the tube before it finally escapes from the one opening still open. The ozone which finally passes from the tubing easily sterilizes the outside of the tubing and all portions of the tubing is sterilized since all possible pockets are eliminated.

This aspect of the invention creates a device which is able to effectively sterilize tubing. Those of ordinary skill in the art readily recognize that an adapter is also effective for sterilizing any hollow article having openings. This would include endoscope handles and other non-tubularly shaped articles.

Although the preferred embodiment utilizes rigid containers in its application, flexible bags are also used. The flexible bags are constructed of a material which is impermeable to contamination and have two ports, an inlet port and an outlet port. In the preferred embodiment, each port is equipped with a valve which permits attachment/detachment between either the ozone generator or an ozone destruct mechanism. Each valve also automatically seals upon detachment.

Additionally, in the preferred embodiment, the valves are pressure activated. The inlet port is opened only when pressure from the ozone generator exceeds a preselected limit. This keeps the contents of the flexible bag sterile until ozone is present.

In a like manner, the outlet port is opened when pressure within the bag exceeds a preselected level. This permits the bag to swell to a point and then release the gas. The induced pressure within the bag keeps the ozone gas under pressure so as to prolong the life of the ozone in the gaseous state or if suspended in a liquid.

In an alternative flexible bag, the bag is equipped with a single opening into which the to-be-sterilized items are placed. A "lid" arrangement is secured to the single opening through a screw-type action. The "lid" has two openings which are selectively open/closed the sterilizing unit. These two openings act as an inlet and an outlet port.

Note that when a flexible bag is used, either an ozone laden gas or an ozone laden liquid is usable as the sterilizing agent. In either case, gas or liquid, the steriliant is passed through the bag and then through the exit port.

Once the sterilization process is completed, the operator removes the bag from the ozone generator and the ozone destruct mechanism and then applies manual pressure on the bag. This "squeezing" of the bag forces excess ozone from the bag through the outlet port's pressure activated valve. In this manner, the bag is shrunk for storage and yet the sterile integrity of the bag's interior is maintained.

An adapter, as discussed above, is also usable by connection to the interior portion of the inlet port. This permits hollow tubes and articles i.e. endoscope handles) to be effectively sterilized within the flexible bag.

Although the use of dry ozone gas is preferred in certain situations, a liquid ozonizated bath is also applicable to certain situations. The present invention provides for an efficient method and apparatus to create this ozonizated bath which is designed to optimize the life and effectiveness of the ozone.

A liquid, such as distilled water, is placed in a pressurized reservoir and ozone gas, as described before, is pumped into the reservoir. Excess gas is vented to keep the reservoir at a preselected pressure level. The ozone gas is diffused into the liquid either directly or through a diffuser mechanism well known to those of ordinary skill in the art. Optionally, the reservoir is also chilled to optimize the suspension of the ozone within the liquid.

One the ozonizated liquid is created, it is usable in any of the applications already discussed. The ozonenated liquid is pumped or released into a container having a material to be sterilized and the excess liquid, together with any debris, is carried to an ozone destruct mechanism such as activated charcoal.

The waste liquid and debris is sterile so it may be disposed of safely through traditional waste water systems such as sewer systems.

This embodiment is particularly useful for the sterilization of materials where a liquid bathing action is preferred due to added contact, agitation for physical removal of contaminates, or for the water's inherit cleansing action.

Agitating of the liquid medium is beneficial and is accomplished through a variety of methods well known to those in the art. Mechanical agitation forces the water to move against the item and thereby remove debris; sonic agitation also dislodges the debris and also forces the suspended ozone gas into a "fiz-type" of state which further encourages the dislodging of debris.

This embodiment of the invention is particularly useful for the cleansing and sterilization of endoscopes which have biological debris attached to them. As example, the cleansing of material from a laparoscope is greatly facilitated by the agitation action.

In this regard, one aspect of the present invention relates to the treatment of flexible, usually woven, materials which have become contaminated with biological wastes. One such application is generated in the medical field associated generally with surgeries; those of ordinary skill in the art readily recognize various other applications which generate a similar type of waste.

In the surgical application, a large number of sponges, bandages, wipes, and the like are generated. These biologically contaminated waste materials are discarded into a receptacle called a "red bag". The red bags are collected from the various points within the hospital and are typically incinerated. The steps between the operating room and final incineration requires numerous handling by humans which increases the potential of infection to these handlers. Additionally, many hospitals are not licensed to have incinerators.

The present invention is a self-contained mechanism which is "wheeled" into the operating room (or other suitable place) next to the surgeon. As with the red bag, the surgeon disposes of the waste by throwing it into the self-contained mechanism's drum's top opening. When the operation is completed, the top of the drum is sealed and the mechanism is "wheeled" into another room. The mechanism is attached to electrical power, a liquid source, and a waste water disposal port. The preferred liquid in this application is distilled water, but, those of ordinary skill in the art readily recognize various other liquids which serve this function.

Once so connected, the mechanism is started. Note that at no time, other than the surgeon, is the waste handled by any human.

In operation, the mechanism creates an ozonenated bath as discussed before and mixes this with a detergent which is pumped into the drum. Through an agitating mechanism, the contents of waste, ozonenated liquid, and detergent, are mixed and agitated so that an initial bathing/sterilization action is performed. In the preferred embodiment, the drum is both pressurized and chilled to increase the life of the ozone.

In this embodiment, water is used to create a bath. This water is either distilled or is filtered so that a maximum life of the ozone gas is obtained. Those of ordinary skill in the art readily recognize other mediums which can be used in this context.

Although the embodiment above discusses the use of detergent with an ozone bath, ozone is also useful to degrade detergent. As such, in one embodiment of the invention, the detergent with water (without ozone) is used as an initial washing action followed by the addition of an ozone bath. This structure provides for not only the cleansing and sterilization, but also a breakdown of the detergent rendering it less harmful for the environment.

Once the initial bath is completed, the residue and liquid are removed from the drum, either through simple pumping action or in combination with a spinning action of the drum. Note that the residue is sterilized and can be discharged without concern for biological contamination. Further, the ozone tends to break down the detergent so that it too does not pose any environmental threats.

Another bath of ozonenated liquid is performed on the waste fabrics in the drum before the waste is acceptable for disposal, or in certain situations, reuse.

This arrangement performs a complete sterilization of the waste material without endangering human operators by requiring any additional handling of The invention, together with various embodiments thereof will be more fully described by the following drawings and their accompanying descriptions.

DRAWINGS IN BRIEF

FIG. 7 is a block diagram of the dry ozone aspect of the present invention.

FIG. 8 is a cutaway view of a flexible bag embodiment of the present invention incorporating an adapter.

FIG. 9 is a close-up cut-away view of the preferred pressure release valve as is used in the flexible bag embodiment.

FIG. 12 is a perspective view of the self-contained mechanism showing its application in a surgical application.

Figure 14A:
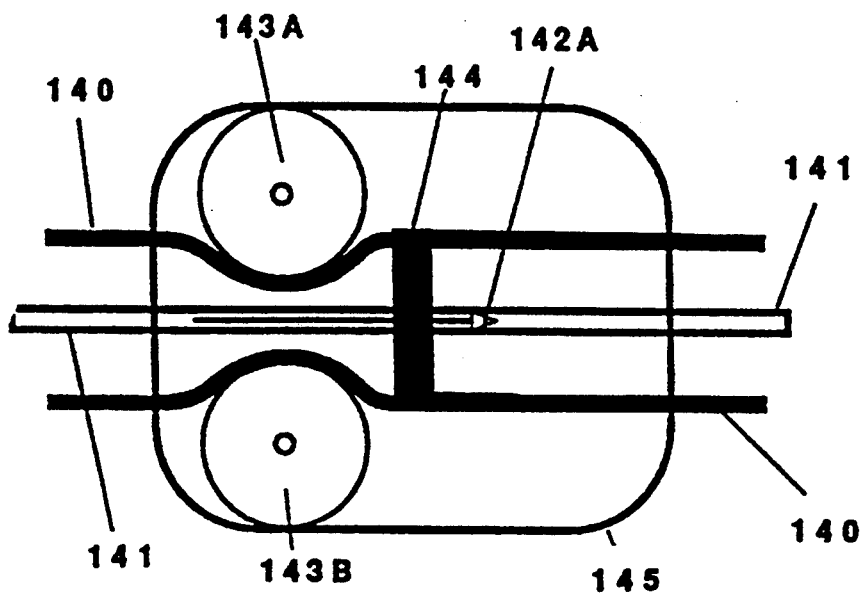
Figure 14B:
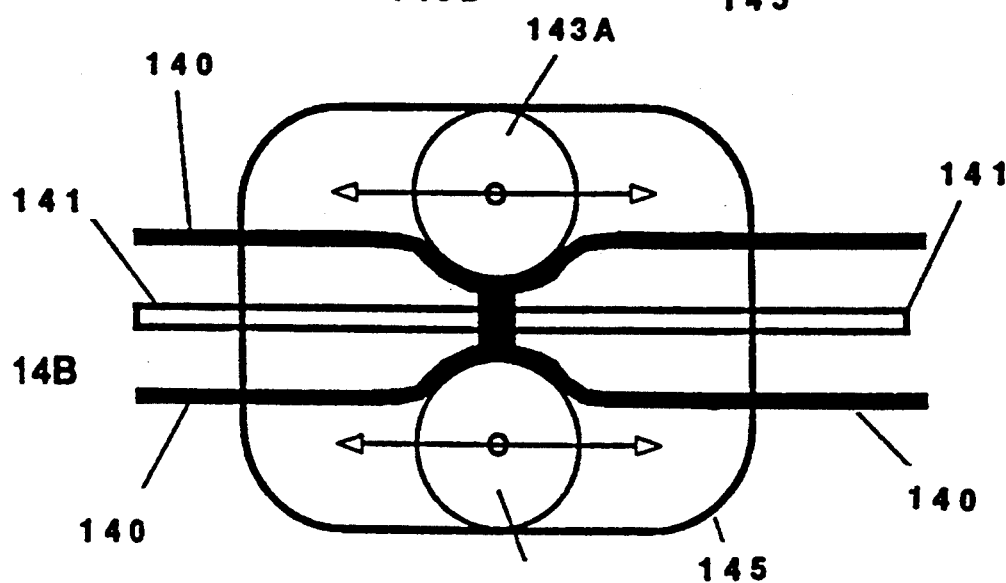
Figure 14C:
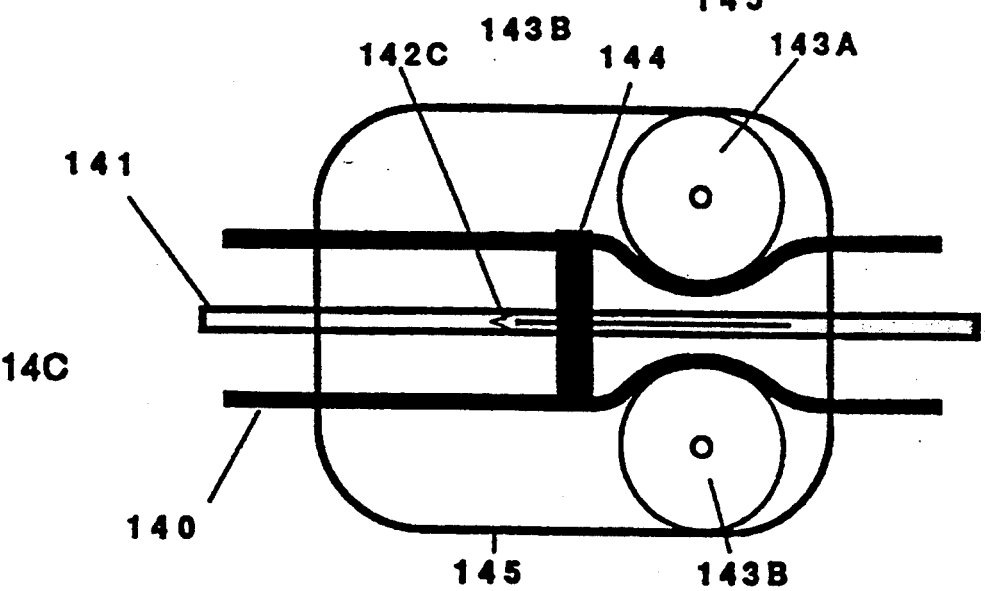

FIGS. 14A, 14B, and 14C illustrate the peristaltic surge washing mechanism.

FIGS. 15A and 15B are end views of the preferred capsule illustrating the rack and the diaphragm.

FIG. 16 is a side view of the mechanism illustrating the tilting action of the preferred embodiment.

Figure 17A:
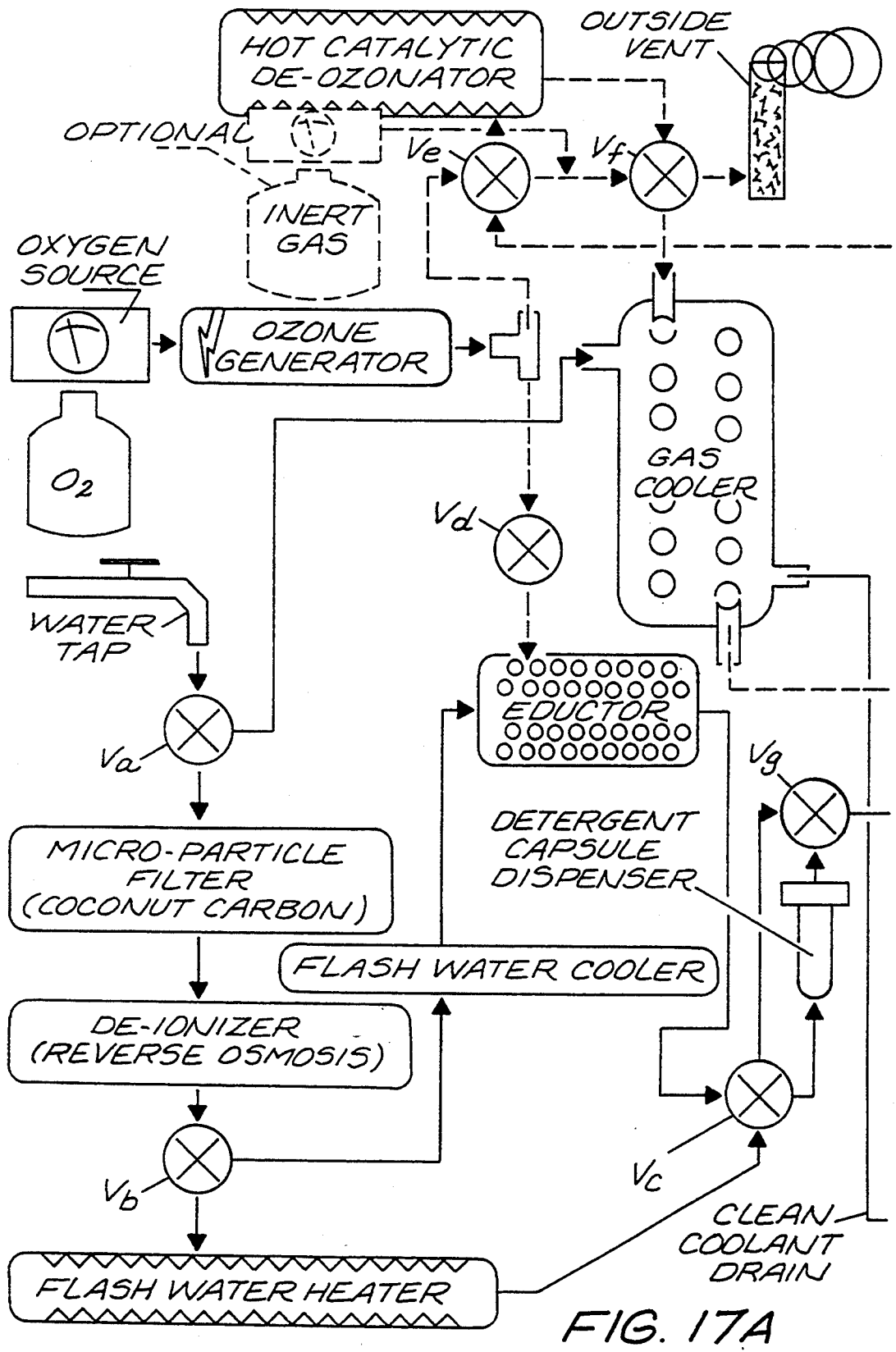
Figure 17B:
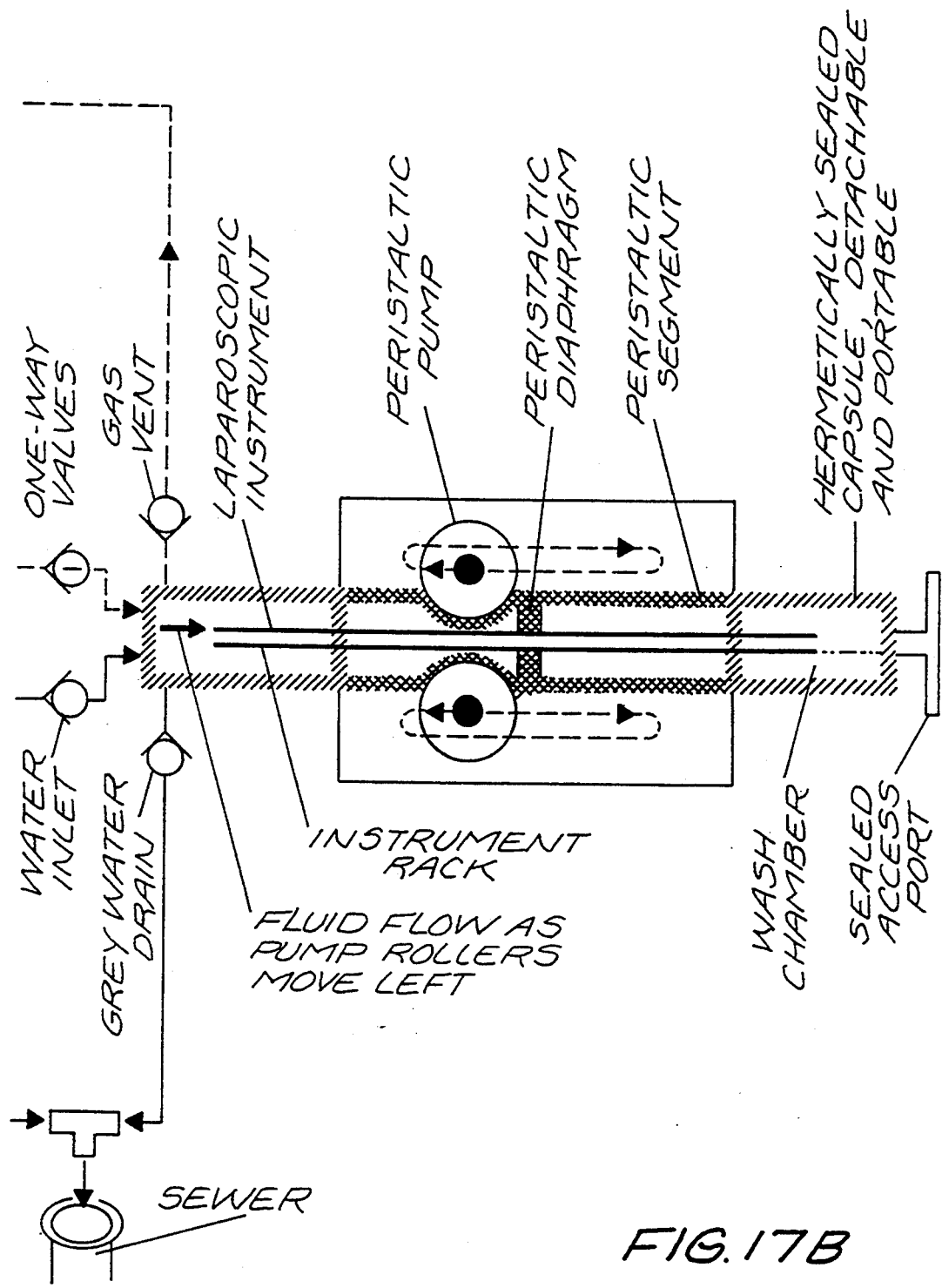

FIGS. 17A and 17B, when taken in conjunction, comprise a functional layout diagram of the preferred embodiment used to clean/sterilize laparoscopic instruments.

FIG. 18 is a perspective view of an embodiment of the endoscope cleaning/sterilizing apparatus.

DRAWINGS IN DETAIL

Figure 1:
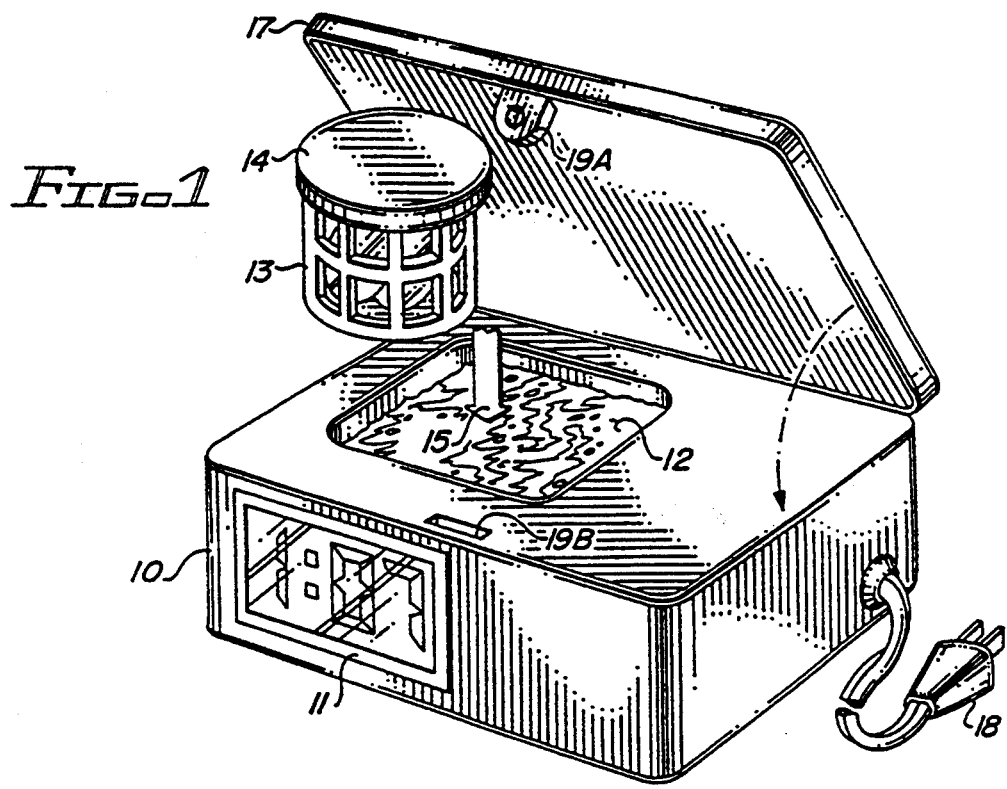
FIG. 1 is a perspective view of a personal use embodiment of the invention.

FIG. 1 is a perspective view of a personal use embodiment of the invention. This embodiment is intended to be used by the contact wearer to periodically clean and disinfect their own contact lenses at home.

Contact lense cleaner 10 receives its power via electrical cord 18 which utilizes household electrical current. This electrical current is used to power clock 11 and the ozone generator (not shown). Clock 11 is a countdown type of clock showing the remaining time necessary for proper cleaning the contact lenses.

The contact lenses are placed in cage 13. To facilitate easy placement of the lenses within cage 13, removable top 14 permits access to the interior portion of cage 13. Cage 13, once the contact lenses are placed therein, is lowered, as illustrated by arrow 15, into basin 12 (having saline therein) and lid 17 is closed, as illustrated by arrow 16.

The closing of lid 17 causes latch 19A to enter receptacle 19B which signals clock 11 that the contact lenses are suitable placed within basin 12. Clock 11 then activates the ozone generator (not shown) to create a bath of ozone and saline within basin 12.

When the selected amount of time has elapsed, clock 11 deactivates the ozone generator and releases lid 17 by latch 19a. The raising of the lid signals the user that the contact lenses are clean and ready for rinsing and use.

In one embodiment of this invention, cage 13 is removable and has a protrusion which supports it above basin 12. This permits the enclosed contact lenses to drip dry and also provide a time lapse for any absorbed ozone to convert to its benign by-products before the user again places the contact lenses within their eyes.

It has been found that through control of the amount of ozone and the amount of time of exposure, contact lenses may not only be cleaned but either disinfected, asepticized, or even sterilized. Control of these factors, amount of ozone and elapsed time, depends upon the manufacturer and user to obtain the desired results.

Figure 2:
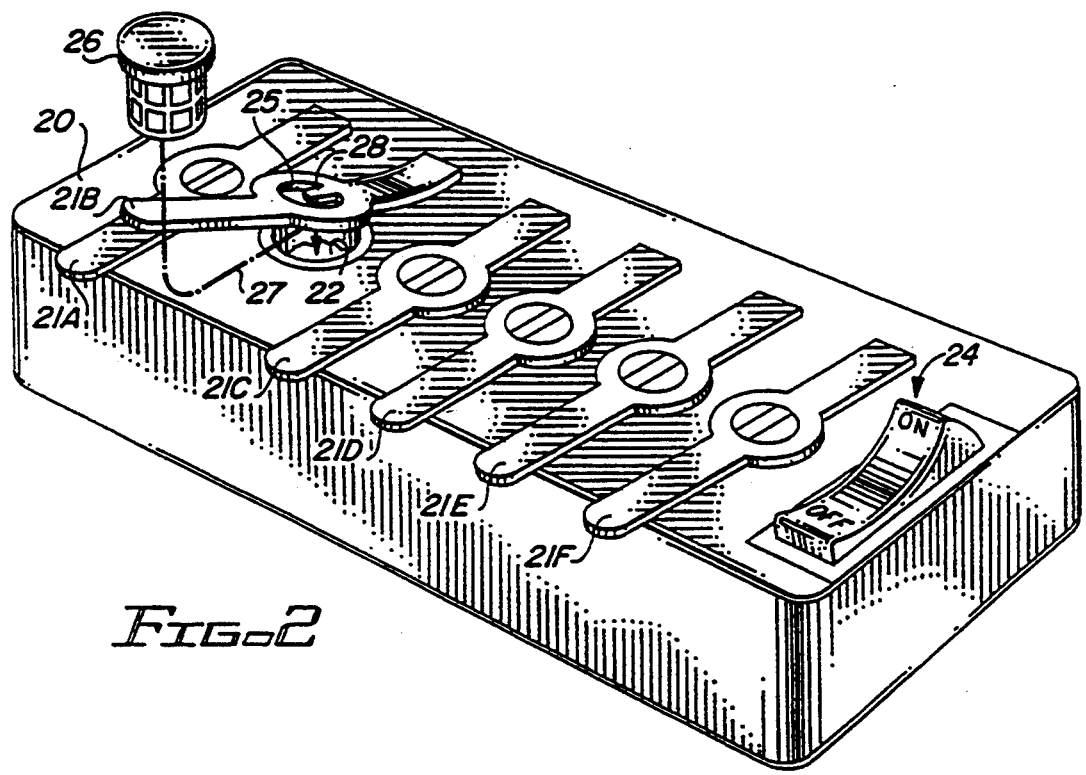
FIG. 2 is a perspective view of a production use embodiment of the invention.

FIG. 2 illustrates an embodiment of the invention for production cleaning. This embodiment is wired into the electrical current of the shop and is activated by a simple on/off switch 24.

Once activated, the bath of ozone and saline contained within unit 20 is created and is constantly fed ozone until the work shift is completed or when the task is completed.

A plurality of holders (21A, 21B, 21C, 21D, 21E, and 21F) are used to clean contact lenses in parallel. Each holder, such as holder 21A, maintains the cage holding the contact lenses in the bath. When the appropriate time has elapsed, the holder raises the cage from the bath.

In this example, holders 21A, 21C, 21D, 21E, and 21F all have cages (such as cage 23 for holder 21A) emersed in the bath. Holder 21B has raised indicating to the operator that cage 26 must have its existing contact lenses removed and another set secured therein.

Once the unclean contact lenses are secured within cage 26, the cage is placed in orifice 25 on holder 21B as indicated by arrow 27. Keeper 28 secures cage 26 in position; the handle of holder 21B is then pushed down forcing secured cage 26 into bath 22.

Keeper 28 is used in this embodiment to secure cage 26 within holder 21B. In another embodiment of the invention, keeper 28 is timed controlled to prevent removal of cage 26 before an allotted amount of time has elapsed for proper drying of the contact lenses.

Those of ordinary skill in the art readily recognize various mechanisms which will work as timing devices for holders 21A, 21B, etc. such as: electronic clocks linked to the holder; spring timed mechanism; and the like.

This embodiment of the invention also illustrates the mechanism which may be used for the personal cleaning apparatus. A mechanism with a single holder is suitable for use by a single user.

Figure 3:
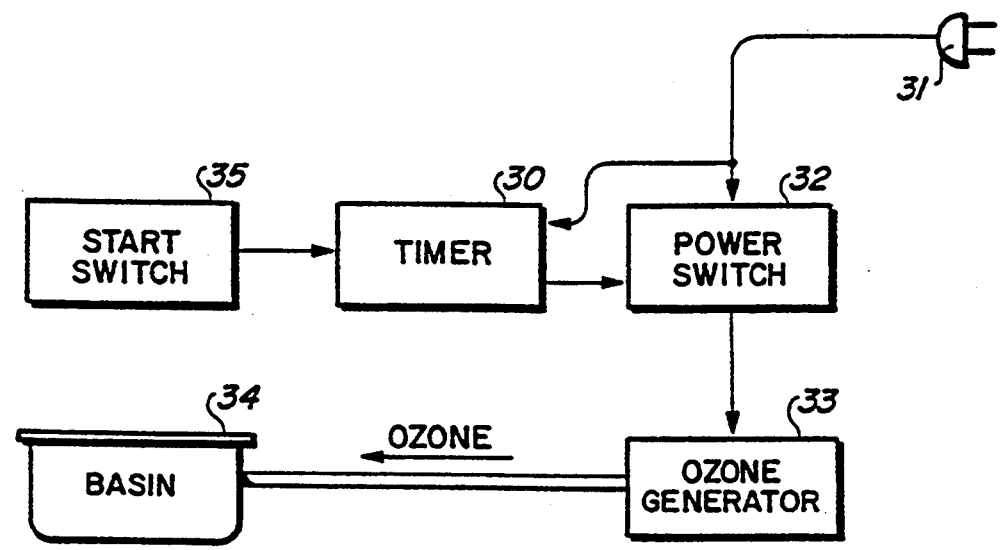
FIG. 3 is a block diagram illustrating the operation of a personal use embodiment of the invention.

FIG. 3 is a block diagram of the operation of an embodiment of the invention. Electrical power is supplied via plug 31 to power switch 32 and timer 30.

Start switch 35 informs timer 30 when the cage holding the contact lenses is properly positioned. Start switch 35 may be a variety of switches well known in the art including the latch switch first illustrated in FIG. 1, a manually operated switch, or any other well known to those in the art.

Once start switch 35 is activated, timer 30, activates ozone generator 33 via power switch 32. Ozone generator provides ozone to basin 34, with saline therein, until such time as timer 30 deactivates the ozone generator 33 by denying electrical power through power switch 32.

It is clear from the foregoing that in this embodiment of the invention, timer 30 acts as a controller for the entire operation of the mechanism.

Figure 4:
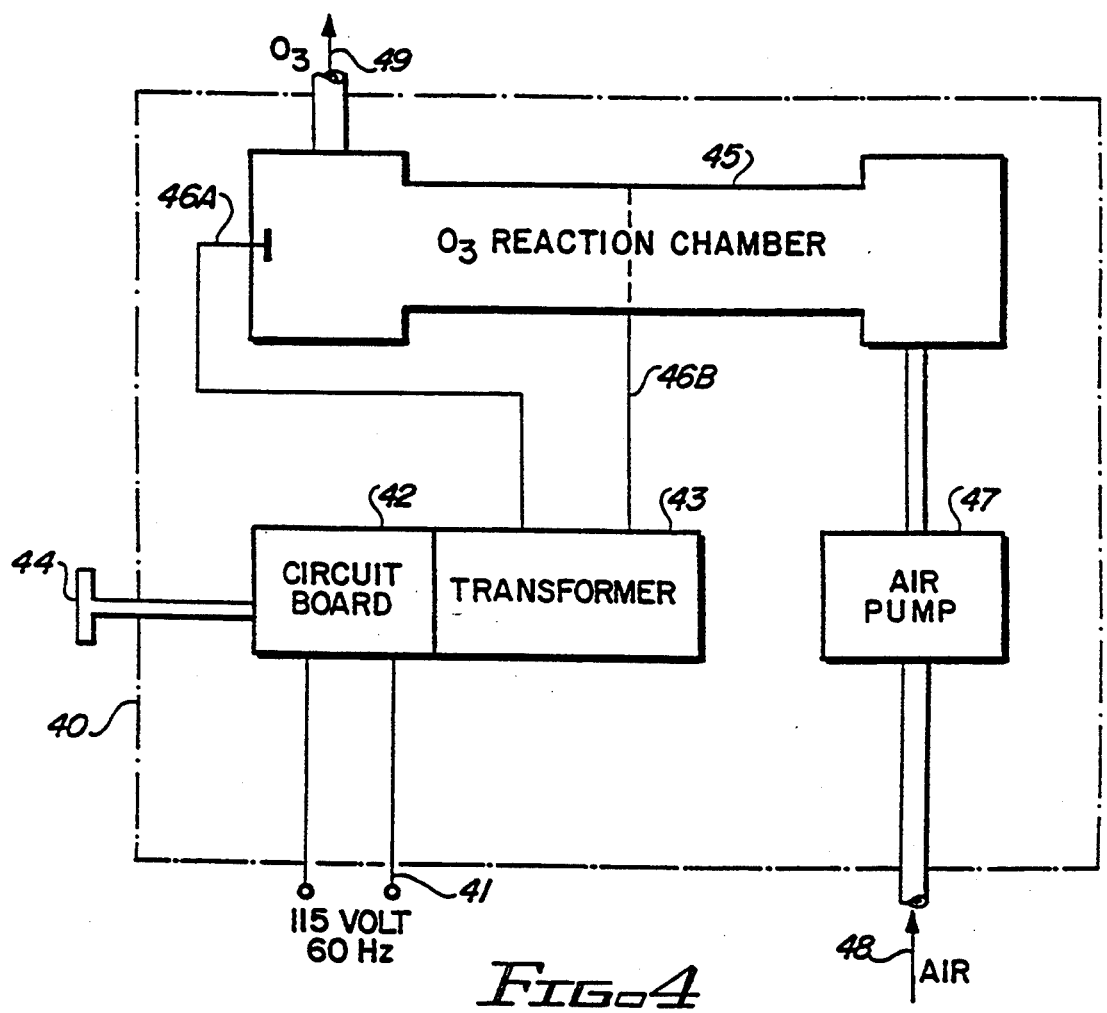
FIG. 4 is a block diagram of the preferred embodiment of the ozone generator.

FIG. 4 is a block diagram of the preferred ozone generator for the invention. Ozone generator 40 receives standard electrical energy 41 being 115 volts at 60 hertz. This electrical energy passes through circuit board 42 and is modified to drive transformer 43 at the prescribed rate as determined by operator adjustment knob 44. Utilizing the operator adjustment know 44, the operator is able to vary the concentration of ozone being produced by ozone generator 40.

Leads from transformer 43 feed a cathode 46A and anode 46B positioned within the ozone reaction chamber 45. Ozone reaction chamber 45 is preferably constructed of stainless steel and has a glass dielectric therein.

Air pump 47 draws in outside air 48 into the system and through ozone reaction chamber 45 producing a flow of ozone 49.

Those of ordinary skill in the art readily recognize alterations which may be made to the present layout to permit this embodiment to be utilized in a variety of settings and for a variety of ozone demands.

Figure 5:
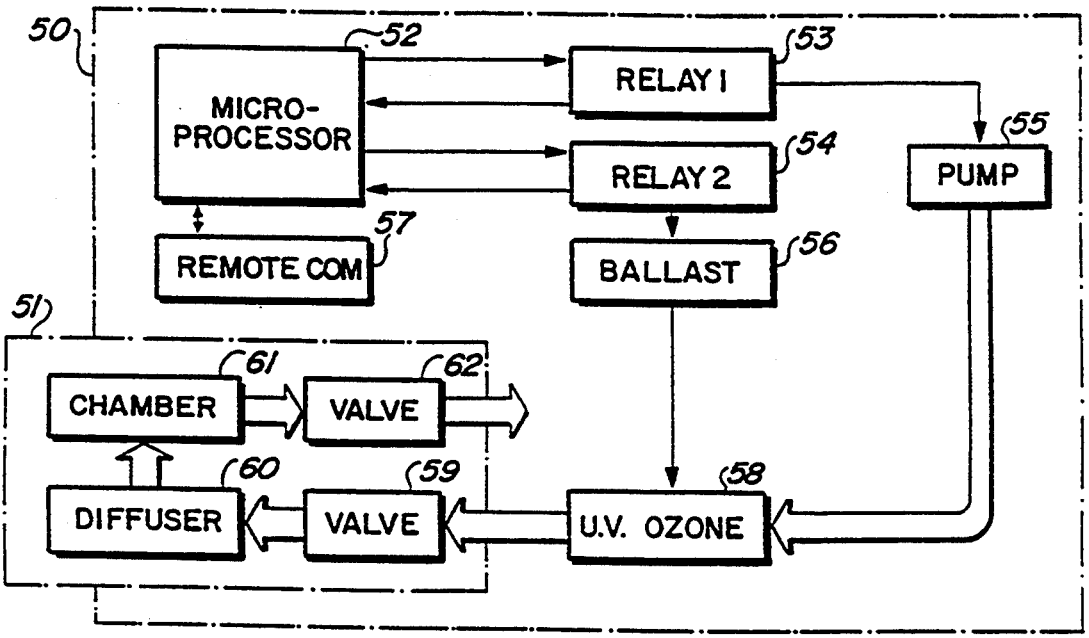
FIG. 5 is a block diagram illustrating the interaction of the components the preferred embodiment of the contact lense cleanser sterilizer.

FIG. 5 is a block diagram illustrating the interaction of the components for the preferred embodiment of the contact lense cleanser/sterilizer.

Main unit 50 receives electrical power (not shown) via a typical house outlet of 110 volt. Microcomputer 52 acts as a controller for the entire unit. By activating relay 1, microcomputer 52 is able to activate pump 55; by activating relay 54, microcomputer is able to activate ballast 56 which energizes the Ultraviolet ozone generator 58.

Air flow from pump 55 is passed through the 6zone generator 58 and ozone is created. The ozonized air flow passes into container 51 via valve 59. Ozone bubbles within the air flow are broken into small bubbles via diffuser 60. Diffusion of the ozone increases the surface area of the ozone and thereby increases the overall effectiveness.

The diffused ozone air flow passes through chamber 61 where the items to-be-cleaned are placed. Finally, the ozone air flow is exhausted via valve 62.

Both valve 59 and valve 62 seal when container 51 is removed from housing 50. Container 51 keeps the contact lenses, or other items, sterile until container 51 is opened.

Microcomputer 52 is able to communicate with a remote computer (not shown) via remote communication link 57. In the preferred embodiment, this remote communication link is a modem type device although those of ordinary skill in the art readily recognize various other mechanism which will serve this purpose.

Memory, located in this embodiment within microcomputer 52, is nonvolatile permitting a constant upgrade of the operational data and also of the time parameters and usage of the device. This information is easily communicated via the remote communication link 57.

Additionally, remote communication 57 permits a remote computer, such as in a physician's office, to reset the device permitting the operator to use the device once his allotted amount of uses has been completed. This practice assures the physician that the user is actually using the device and also forces the user to come in for scheduled reexamination to assure that the contact lense is not causing some unforeseen-damage to the eye.

Microcomputer 52 is able to monitor, via sensors (not shown) the operation of pump 55, ballast 56, ozone generator 58, and that container 51 is securely placed within housing 50. So long as everything is operating within specifications, microcomputer operates the assemblage until the predetermined amount of time has elapsed.

Should one of the components malfunction, then microcomputer terminates operation and informs the operator of the aborted operation.

Should the application require, a filter is added to valve 62 to trap excess ozone from entering the atmosphere.

Figure 6:
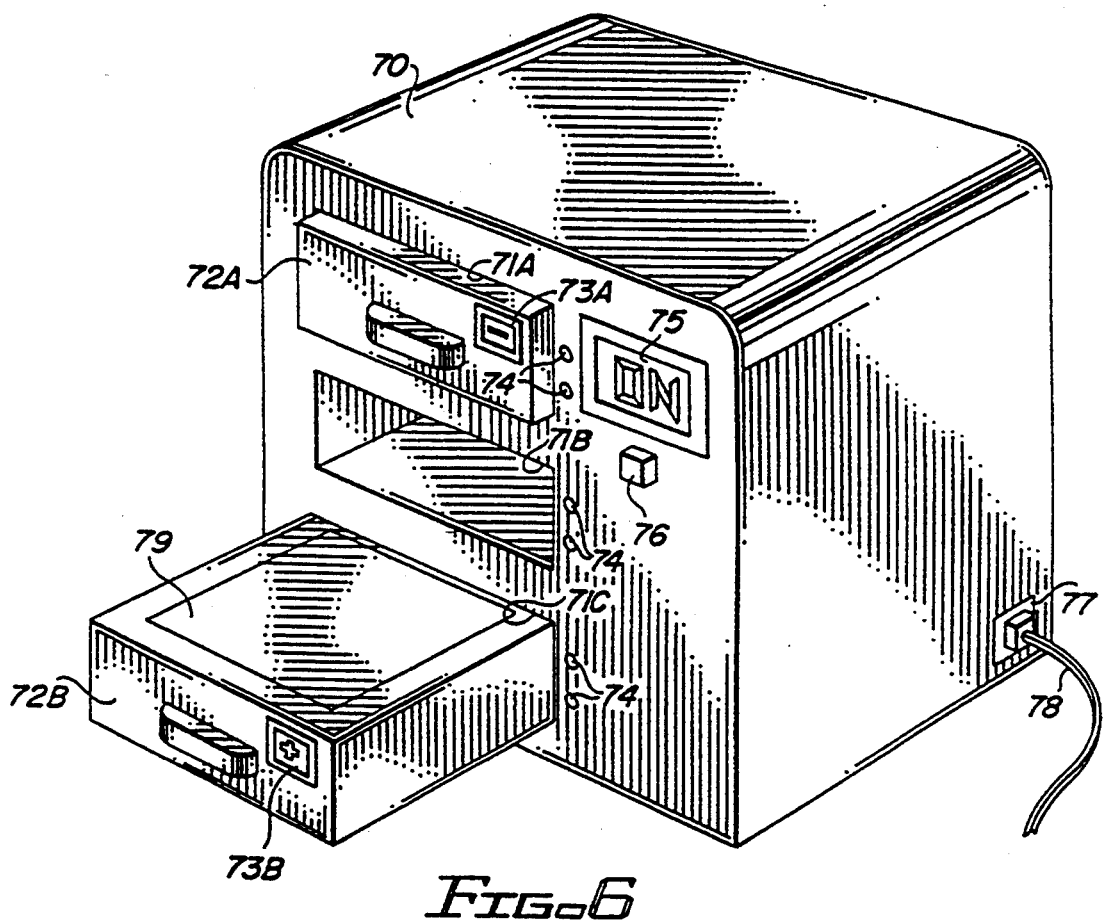
FIG. 6 is a perspective view of an embodiment of the invention utilizing multiple container capability.
Figure 10A:
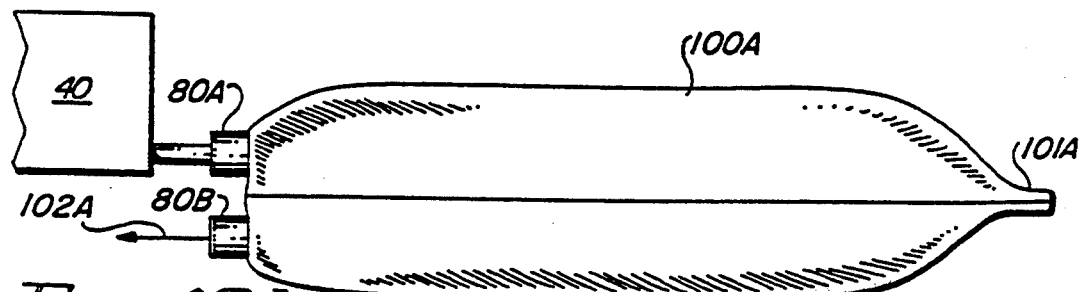
FIGS. 10A–10E are side views of a flexible bag embodiment in use.
Figure 10B:
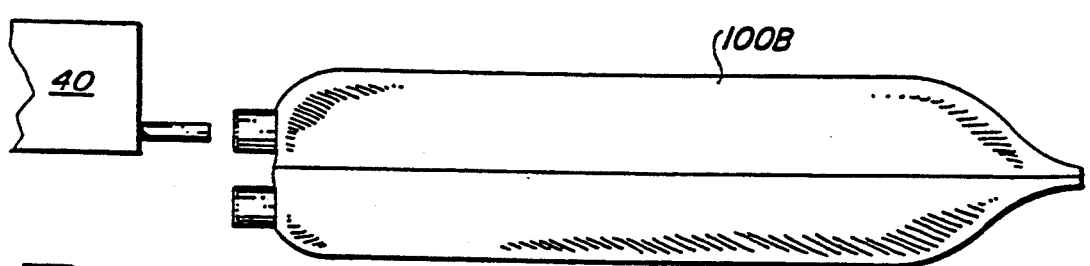
Figure 10C:
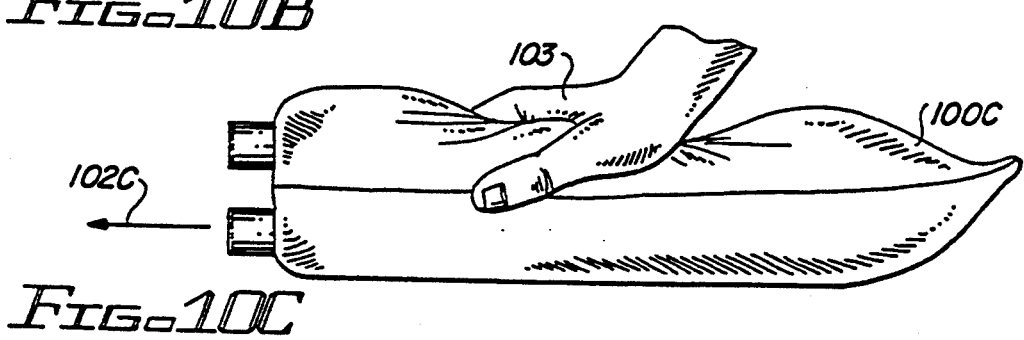
Figure 10D:
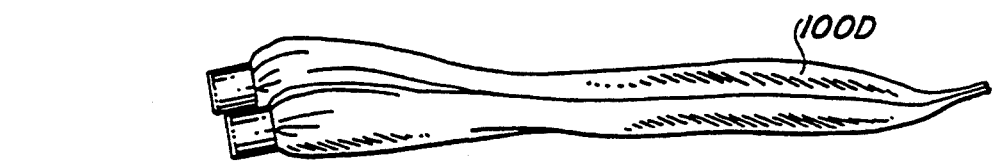
Figure 10E:
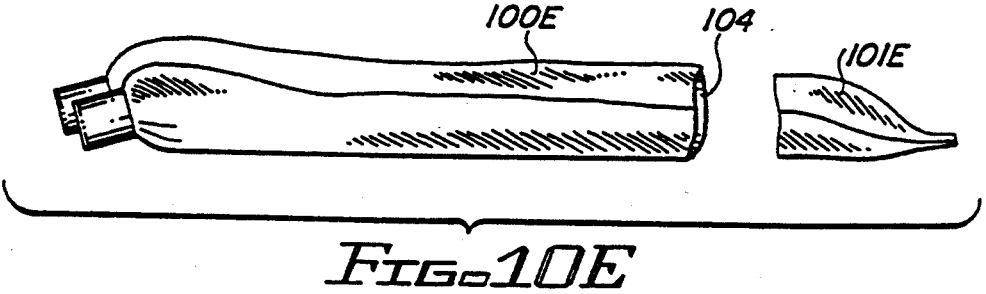

FIG. 6 is a perspective view of an embodiment of the invention utilizing multiple container capability.

Housing 70 contains multiple slots 71A, 72B, and 71C. Although this embodiment illustrates three slots, those of ordinary skill in the art readily recognize that any number of slots is possible.

Into these slots are inserted containers 72A and 72B. Note that slot 71B is empty at the present time. In this embodiment, once a container has had its contents sterilized, it may be removed and stored without contaminating the contents since the valves (not shown) are self-sealing and lid 79 is also sealed.

As an added contamination safeguard, indicators 73A and 73B are used to indicate if the contents are sterile or not. The microcomputer (not shown) moves indicator 73B to a "+" indicating that the sterilization process in complete; opening of the lid moves indicate to a "−" (as shown in 73A. In this fashion, a sterile container is easily identified.

Status display 75 is used by the microcomputer to communicate with the operator. Switch 76 permits the operator to activate/deactivate the device.

Communication with remote computers is facilitated via modular jack 77 and phone line 78.

FIG. 7 is a block diagram of the dry ozone aspect of the present invention.

Oxygen gas is supplied from a pressure vessel, illustrated in this example as a pressurized bottle 63, to ozone generator 40. Ozone generator 40 converts some of the oxygen gas into ozone resulting in an oxygen/ozone mixture being delivered to flexible bag 64.

Flexible bag 64 contains an instrument 67 therein which is exposed to the oxygen/ozone gas mixture 68 which circulates within flexible bag 64 and then exits, 69, to ozone destruction mechanism 65 before being exhausted into the atmosphere 66.

Ozone destruction mechanism 65 is any one of many well known to those of ordinary skill in the art including, but not limited to, activated charcoal filters.

In this embodiment, the dry ozone gas so generated is particularly useful for metal instruments and for sharpened instruments where heat would dull their edge.

FIG. 8 is a cutaway view of a flexible bag embodiment of the present invention incorporating an adapter.

Flexible bag 64, in this embodiment, is constructed of two sheets of impermeable material, well known to those of ordinary skill in the art, which are sealed around the periphery. An inlet port 80A and an outlet port 80B permit the introduction and exhausting, respectively, of ozone gas. Connectors, such as connector 86, press into and seal with ports, permitting ozone to be communicated, as illustrated by arrow 84B.

The ozone stream passes valve 85A, and in this embodiment, pass into adapter 81. Adapter 81 attaches to the interior side of input port 80A. In this illustration, adapter 81 has three connectors, 82A, 82B, and 82C, which connect to three openings in tube 83. Ozone gas is thus forced into each opening to pass through the entirety of the tube 83 and finally exit from end 87 as illustrated by arrow 84A. In this manner, the ozone fully sterilizes the interior of tube 83 and the ozone then proceeds to sterilize the exterior of tubing 83 once it exits.

When pressure within the flexible bag 64 reaches a selected level, valve 85B of outlet port 80B opens permitting the gas to escape as illustrated by arrow 84C. Valve 85B is important in that it maintains pressure within flexible bag 64 so as to increase the life and effectiveness of the ozone, and also assures that no inward flow is permitted through the outlet port 80B; this latter attribute prevents contamination of the interior of bag As those of ordinary skill in the art recognize, the flexible bag, configured with the inlet port and outlet port with associated valves, is applicable to a variety of situations where a steriliant, other than ozone, is used.

In an alternative flexible bag, the bag is equipped with a single opening into which the to-be-sterilized items are placed. A "lid" arrangement is secured to the single opening through a screw-type action. The "lid" has two openings which are selectively open/closed the sterilizing unit. These two openings act as an inlet and an outlet port.

In this embodiment, the valves are not pressure activated but seal upon removal of the bag from the ozone generator.

Note that when a flexible bag is used, either an ozone laden gas or an ozone laden liquid is usable as the sterilizing agent. In either case, gas or liquid, the steriliant is passed through the bag and then through the exit port.

FIG. 9 is a close-up cut-away view of the preferred pressure release valve as is used in the flexible bag embodiment. Those of ordinary skill in the art readily recognize various other valves which are useful in this application including a shut-off valve found in various applications.

Although FIG. 9 illustrates an outlet port valve, those of ordinary skill in the art readily recognize that by simply turning the valve to face the other direction, the same valve is useable as the inlet port's valve.

Inlet port 80B is constructed to have shoulders 90 imposed therein. Ball 91 seals the opening between shoulders 90 and is retained by post 92 and spring 93. As pressure within chamber 94, fed from the flexible bag-not shown in this figure, increases, the force exerted on ball 91 increases until such time that the pressure overcomes the force from spring 93 permitting some internal gas to escape until such time that the pressure is reduced to a point where spring 93 may again reseal the valve.

Through proper adjustment in the engineering of spring 93 and the length of post 92, the level of pressure necessary to open the ball 91/shoulder 90 combination is adjusted.

This valve permits the controlled exhausting of gas without any reverse flow which would cause contamination within the flexible bag.

An alternative port arrangement doesn't use pressurized valves but instead relies upon valves which are automatically opened by the ozone generator after ozone steriliant begins to flow and which closes the valves prior to the shut-down of the ozone steriliant. Those of ordinary skill in the art readily recognize various mechanisms which accomplish this objective.

FIGS. 10A–10E are side views of a flexible bag embodiment in practical use.

As discussed earlier, ozone generator 40 passes ozone via input port 80A into the flexible bag causing it to inflate, 100A. One end of the flexible bag is sealed, 101A. Sealing of the bag is accomplished through a variety of methods well known to those of ordinary skill in the art, including but not limited to, the formation of a resealing mechanism in which a bead on one edge is securable to a bead locking mechanism. In this embodiment, the sealing is through heat melding of the sides of the flexible bag to each other.

Flexible bag 100B is detached from the ozone generator 40 and is deflated through manual pressure 103. Manual pressure 103 forces gas 102C through the outlet port of bag 100C so that the bag becomes smaller 100D and easier to store and move. Flexible bag 100D is stored and easily handled without losing the sterile integrity of the bag.

When the operator is ready to use the contents of bag 100D, the end 101E of the bag 100E is cut off, 101E, resulting in opening 104 from which the sterile instruments are removed. In this manner, the instruments are kept sterile until such time that they are used.

Should the user wish to reuse bag 100E, then by simply placing the contaminated instruments into the bag via opening 104 and resealing the opening, through a heat sealing operation, the bag is reused several times.

Figure 11:
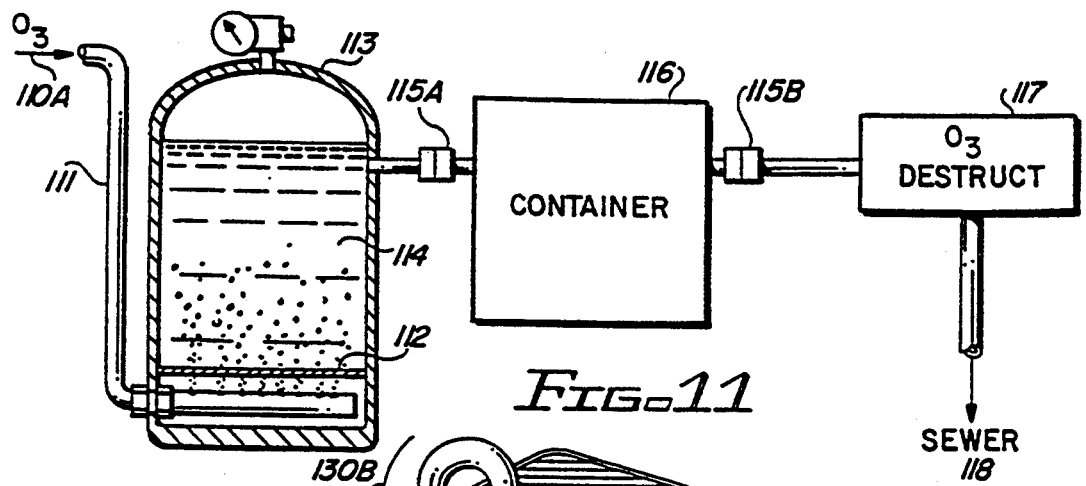
FIG. 11 is a block diagram of the creation of ozonenated liquid and its use in sterilization.

FIG. 11 is a block diagram of the creation of ozone-nated liquid and its use in sterilization.

In many situations, there is a need for a liquid sterilizing agent. The embodiment of FIG. 11 creates such a source of ozone. By applying ozone gas under pressure 110A to pipe 111, the ozone is forced into bath 114 within reservoir 113. In this embodiment, reservoir 113 is sealed for pressurization and is chilled (not shown) to prolong the life of the suspended ozone within the water. Also, in this embodiment, distilled water is used as the liquid medium, but those of ordinary skill in the art readily recognize various other liquids which will work in this application.

The gaseous ozone is passed through diffuser 112 into the water and is suspended therein. Excess gas is vented so that pressure within the reservoir is kept within tolerances of the container.

Once the water has been fully charged with ozone, the ozonenated water is passed through connect valve 115A to container 116 for sterilization of the contents.

Connect valve 115B permits container 116 to be removed from the ozone destruct mechanism 117.

Spent liquid from the ozone destruct mechanism 117 is discharged to the sewer 118.

FIG. 12 is a perspective view of the self-contained mechanism showing its application in a surgical application.

This embodiment has applications to operating rooms, dressing stations, maternity rooms, and delivery rooms. Anywhere there is a large volume of biologically contaminated material generated, this embodiment is useful.

Within the operating theater, a large amount of biologically contaminated waste is generated which must be either destroyed or sanitized. This self-contained mechanism permits the surgeon 120 to toss such contaminated material directly into a drum within mechanism 121 via top opening 122.

The self-contained mechanism is later wheeled into a room for treatment.

Figure 13:
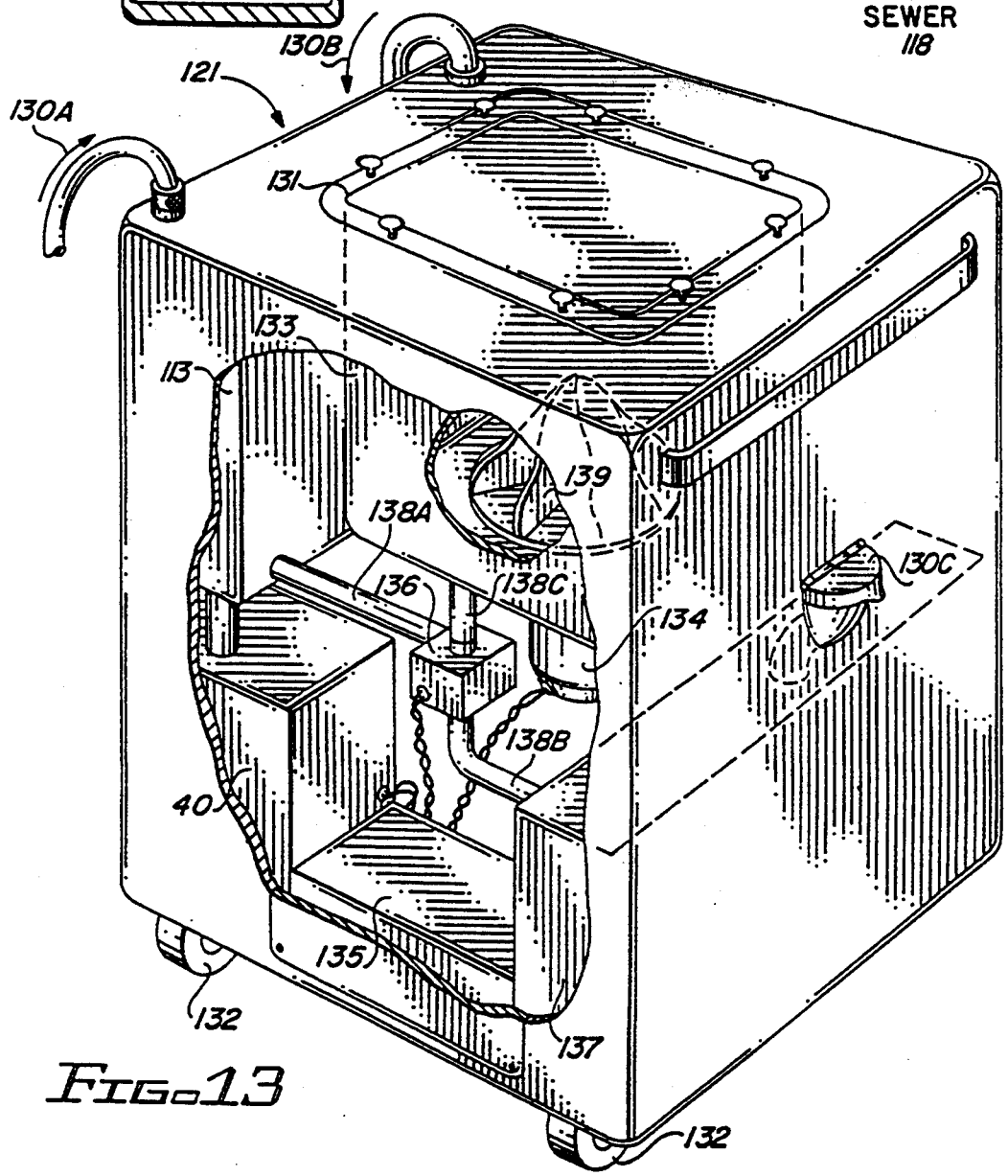
FIG. 13 is a cut-away view of the preferred self-contained mechanism showing the components thereof.

FIG. 13 is a cut-away view of the preferred self-contained mechanism showing the components thereof.

Container 121 has it's drum 133 sealed via lid 131. Lid 131 helps to maintain pressurization of drum 133. Note, no human handling of the contaminated material is required. Mechanism 121 is easily moved from the operating room to another location via wheels 132.

Once so sealed, mechanism 121 is attached to a water source 130A, a waste disposal source 130B, and an electrical source (not shown). Activation of the mechanism causes water reservoir 113 to be charged with ozone from ozone generator 40. In the preferred embodiment, reservoir 113 is pressurized and chilled to a selected temperature.

The operator fills a detergent reservoir 137 via fill hole 130C.

In the preferred embodiment, water source 170A flows though filter 140 which removes suspended particles and provides a relatively pure source of water to the mechanism 121. Filter 140 is preferably constructed of a coconut carbon with silver impregnated carbon with cation and anion resins so that maximum filtration is obtained.

Computer 135 controls the timing and operation of the entire mechanisms. Using valve block 136, and piping 138A, 138B, and 138C, the computer directs the following sequential operation:
1) drum 133 is filled with a bath mixture of ozonenated water (reservoir 113) with detergent (detergent reservoir 137) {note, in some embodiments, this step is broken into two components- a detergent bath followed by an ozone bath to sterilize and break-down the detergent};
2) motor 134 causes agitator 139 to agitate the liquid mixture and contaminated fabric material within drum 133;
3) the bath and residue from drum 133 is pumped (not shown) from drum 133 to the waste disposal via waste hook-up 130B;
4) drum 133 is filled with a bath of ozonenated water from reservoir 113;
5) motor 134, via agitator 139, agitates the contents of drum 133;
6) drum 133 is emptied of all liquid and residue.

In one embodiment of the invention, drum 133 is chilled to extend the life of ozone therein and thereby obtain an enhanced sterilizing operation. Additionally, in another embodiment, drum 133 is spun to help dislodge liquid from the fabrics within drum 133.

In this manner, the contaminated fabrics are cleaned and sterilized permitting the now sterilized fabrics to be disposed in any traditional means and even to be susceptible for reuse.

Note that the operator of the mechanism is not required to touch, handle, or physically move the contaminated material except while it is contained with the drum. The risk to the operator of becoming ill due to the is reduced to a bare minimum.

FIGS. 14A, 14B, and 14C illustrate the peristaltic surge washing mechanism.

Referring to FIG. 14A, once pump frame 145 is secured over the peristaltic membrane 140 holding the laparoscopic instrument 141 (in this example), rollers 143A and 143B engage and depress the peristaltic membrane 140. Liquid within the membrane is squeezed by lateral motion of rollers 143A and 143B forcing the liquid to "escape" from that section of the membrane in the direction of the motion. This escape is via the interior of the laparoscopic instrument 141, as indicated by fluid flow 142A.

Although in this example a laparoscopic instrument is cleaned and sterilized, the invention is capable of cleaning and sterilizing any hollow tubing. The preferred application is for endoscopic instrument cleaning and sterilizing.

Diaphragm 144 creates two sections within membrane 140 and permits the pumping action to force liquid/gas through the hollow Laparoscopic instrument 141.

As the rollers 143A and 143B move to the left in FIG. 14A, the fluid flow 142C through the instrument is to the right. When the rollers 143A and 143B reverse direction and move toward the right, the fluid flow 142C, through the instrument, is toward the left as shown in FIG. 14C. FIG. 14B shows how the membrance 144, compresses as the rollers pass over it.

In this manner, the rollers 143A and 143B "rock" back and force causing surges of liquid sterilant occur within the interior and on the exterior of the enclosed laparoscope. This surging of the liquid causes debris to be dislodged and causes the sterilizing agent, ozone in the preferred embodiment, to reach every crevice within the endoscope, thereby assuring total sterilization.

One extremely interesting observation which has been made in the device is that the rollers need not pass over the diaphragm to cause this surging affect. The oscillating movement of rollers, even in areas remote from the diaphragm, is enough to cause the surging of the liquid through the endoscope.

FIGS. 15A and 15B are end views of the preferred capsule illustrating the rack and the diaphragm.

Peristaltic tube 140 has a generally oval 150 cross-section in this embodiment so as to reduce the overall volume. Rack 151 within the peristaltic tube 140 holds the endoscope (a laparoscopic instrument 152 in this example) for the cleaning process. As shown, laparoscopic instrument 152 is laid within the peristaltic tube 140 and has placed around it's midpoint the disposable diaphragm 144. This diaphragm 144 also effectively defines two different sections within the peristaltic tube 140 with the only liquid access between the sections being the interior of the laparoscopic instrument 152 itself.

Hence, as pressure from the moving roller squeezes the peristaltic zone and reduces the volume in one section of the capsule, the liquid therein can only escape by flowing through the tube/endoscope to the other section. As the roller moves toward the second section, a reverse flow occurs within the instrument 152. This surging through the tubing dislodges debris and assures that the liquid (either a washing mixture, rinsing mixture, sterile gas, or a sterilant) reaches every area of the tubing.

The action of the peristaltic pump is such that it is not necessary for the rollers to actually pass over the diaphragm as shown in FIG. 14B. Rather, diaphragm 144 needs only to be placed somewhere between the ends of the laparoscopic instrument 141.

FIG. 16 is a side view of the mechanism illustrating the tilting action of the preferred embodiment for cleaning/sterilizing endoscopes.

Tube 140 is held on a tilt table (not shown). By ways of couplings 160 for gas and 161 for liquids, gas or liquid is introduced to, or withdrawn from the interior of the peristaltic tube 140. Pump frame 145 is positioned substantially at the center of gravity of the assemblage.

The endoscope is put into the peristaltic tube 140 via sealable opening 163. After tube 140 is sealed, it is rotated to obtain the desired angle, as shown by position 162A and 162B. This movement of position facilitates the filling or draining of liquids to and from the peristaltic tube 140.

Valves 160 and 161 are designed to automatically seal upon release. This assures that the pressurized contents of peristaltic tube 140 remains sterile even after removal of tube 140 from the apparatus.

FIGS. 17A and 17B, when taken in conjunction, comprise a functional layout diagram of the preferred embodiment used to clean/sterilize laparoscopic instruments.

This mechanism permits three different wash/rinse/sterilize cycles (A, B, and C) which vary in the sequence in which the oxidant/sterilant (preferably ozone) is introduced into the system.

In the preferred embodiment, the operator chooses the cycle and then the mechanism automatically performs.

These cycles are generally:

CYCLE A

A.1: Fill the wash chamber, and soak the instruments with filtered ozonated water agitated by the peristaltic pump to denature any protein contaminants: Tilt the Wash Chamber Capsule clockwise; open the Water Tap; Va to Filters; Vb through Flash Water Cooler to Eductor liquid inlet; Vc from Eductor outlet to Vg; Vg from Vc to Water Inlet; open the Water Inlet; Vd to Eductor gas inlet; open Gas Vent to Ve; Ve from Gas Vent to Vf; Vf from Ve to Outside Vent; tilt the Wash Chamber Capsule back to horizontal; close Water Inlet and Gas Vent; activate the Peristaltic Pump.

A.2: Drain the Soak water by injecting sterile Oxygen gas or sterile Inert gas: Stop the Peristaltic Pump; tilt the Wash Chamber Capsule counterclockwise; Va to Gas Cooler to Clean Coolant Drain; Ve from Ozone Generator to Hot Catalytic Deozonator; Vf from Hot Catalytic Deozonator (or from the Inert Gas source in an alternate embodiment) through Gas Cooler to Gas Inlet; open the Gas Inlet; open the Gray Water Drain. Upon completion, close the Gas Inlet and Gray Water Drain.

A.3: Wash with detergent in warm filtered water agitated by the peristaltic pump: Tilt the Wash Chamber Capsule clockwise; Vb through Flash Water Warmer to Vc; Vc from Flash Water Warmer through Detergent Capsule Dispenser to Vg; Vg from Dispenser to Water Inlet; open the Water Inlet; open the Gas Vent: Ve from Gas Vent to Vf; Vf from Ve to Outside Vent; tilt the Wash Chamber Capsule Back to horizonal; Close the Water Inlet and the Gas Vent; activate the Peristaltic Pump.

A.4: Drain the Wash water by injecting sterile Oxygen gas or sterile Inert gas: Stop the Peristaltic Pump; tilt the Wash Chamber Capsule counterclockwise; Va to Gas Cooler to Clean Coolant Drain; Ve from Ozone Generator to Hot Catalytic Deozonator; Vf from Hot Catalytic Deozonator (or from the Inert Gas source in an alternate embodiment) through Gas Cooler to Gas Inlet; open the Gas Inlet; open the Gray Water Drain. Upon completion, close the Gas Inlet and the Gray Water Drain.

A.5: Rinse the instruments with filtered ozonated water agitated by the peristaltic pump to sterilize all surfaces inside and out and to flush any remaining bio-debris: Tilt the Wash Chamber Capsule clockwise; open the Water Tap; Va to Filters; Vb through Flash Water Cooler to Eductor liquid inlet; Vc from Eductor outlet to Vg; Vg from Vc to Water Inlet; open the Water Inlet; Vd to Eductor Gas Inlet; open Gas Vent to Ve; Ve from Gas Vent to Hot Catalytic Deozonator to Vf; Vf from Hot Catalytic Deozonator to Outside Vent; tilt the Wash Chamber Capsule back to horizontal; Close the Water Inlet and the Gas Vent; activate the Peristaltic Pump.

A.6: Drain the Rinse water by injecting sterilizing Ozone gas or sterile Oxygen gas or sterile Inert gas: Stop the Peristaltic Pump; tilt the Wash Chamber Capsule counterclockwise; Va to Gas Cooler to Clean Coolant Drain; Ve from Ozone Generator to Vf; Vf from Ve through Gas Cooler to Gas Inlet; open the Gas Inlet; open the Gray Water Drain. Upon completion, close the Gas Inlet and the Gray Water Drain.

A.7: Repeat the Rinse Cycle (A.5 & A.6) multiple times.

Cycle B

B.1: Wash with Detergent in cool filtered ozonated water agitated by the peristaltic pump: Tilt the Wash Chamber Capsule clockwise; open the Water Tap; Va to filters; Vb through Flash Water Cooler to Eductor liquid inlet; Vc from Eductor outlet through Detergent Capsule Dispenser to VG; VG from Dispenser to Water Inlet; open the Water Inlet; open the Gas Vent: Ve from Gas Vent to Hot Catalytic Deozonator to Vf; Vf from Hot Catalytic Deozonator to Outside Vent; tilt the Wash Chamber Capsule back to horizontal; close the Water Inlet and the Gas Vent; activate the Peristaltic Pump.

B.2: Drain the Wash water by injecting sterilizing Ozone gas: Stop the Peristaltic Pump; tilt the Wash Chamber Capsule counterclockwise; Va to Gas Cooler to Clean Coolant Drain; Ve from Ozone Generator to Vf; Vf from Ve through Gas Cooler to Gas Inlet; open the Gas Inlet; open the Gray Water Drain. Upon completion, close the Gas Inlet and the Gray Water Drain.

B.3: Rinse the instruments with filtered ozonated water agitated by the peristaltic pump to sterilize all surfaces inside and out and to flush any remaining bio-debris: Tilt the Wash Chamber Capsule clockwise; open the Water Tap; Va to Filters; Vb through Flash Water Cooler to Eductor liquid inlet; Vc from Eductor outlet to Vg; Vg from Vc to Water Inlet; open the Water Inlet; Vd to Eductor gas inlet; open Gas Vent to Ve; Ve from Gas Vent to Hot Catalytic Deozonator to Vf; Vf from Hot Catalytic Deozonator to Outside Vent; tilt the Wash Chamber back to horizontal; Close the Water Inlet and the Gas Vent; activate the Peristaltic Pump.

B.4: Drain the Rinse water by injecting sterilizing Ozone gas or sterile Oxygen gas or sterile Inert gas: Stop the Peristaltic Pump; tilt the Wash Chamber Capsule counterclockwise; Va to Gas Cooler to Clean Coolant Drain; Ve from Ozone Generator to Vf; Vf from Ve through Gas Cooler to Gas Inlet; open the Gas Inlet; open the Gray Water Drain. Upon completion, close the Gas Inlet and the Gray Water Drain.

B.5: Repeat the Rinse Cycle (B.3 & B.4) multiple times.

Cycle C

C.1: Wash with Detergent in warm filtered water agitated by the peristaltic pump: Tilt the Wash Chamber Capsule clockwise; Vb through Flash Water Warmer to Vc; Vc from Flash Water Warmer through Detergent Capsule Dispenser to Vg; Vg from Dispenser to Water Inlet; open the Water Inlet; open the Gas Vent: Ve from Gas Vent to Vf; Vf from Ve to Outside Vent; tilt the Wash Chamber Capsule back to horizontal; Close the Water Inlet and the Gas Vent; activate the Peristaltic Pump.

C.2: Drain the Wash water by injecting sterile Oxygen gas or Inert gas: Stop the Peristaltic Pump; tilt the Wash Chamber Capsule counterclockwise; Va to Gas Cooler to Clean Coolant Drain; Ve from Ozone Generator to Hot Catalytic Deozonator; Vf from Hot Catalytic Deozonator (or from the Inert Gas source in an alternate embodiment), through Gas Cooler to Gas Inlet; open the Gas Inlet; open the Gray Water Drain. Upon completion, close the Gas Inlet and the Gray Water Drain.

C.3: Rinse the instruments with filtered ozonated water agitated by the peristaltic pump to sterilize all surfaces inside and out and to flush any remaining bio-debris: Tilt the Wash Chamber Capsule clockwise; open the Water Tap; Va to Filters; Vb through Flash Water Cooler to Eductor liquid inlet; Vc from Eductor outlet to Vg; Vg from Vc to Water Inlet; open the Water Inlet; Vd to Eductor gas inlet; open Gas Vent to Ve; Ve from Gas Vent to Hot Catalytic Deozonator to Vf; Vf from Hot Catalytic Deozonator to Outside Vent; tilt the Wash Chamber Capsule back to horizontal; Close the Water Inlet and the Gas Vent; activate the Peristaltic Pump.

C.4: Drain the Rinse water by injecting sterilizing Ozone gas or sterile Oxygen gas or sterile Inert gas:

Stop the Peristaltic Pump; tilt the Wash Chamber Capsule counterclockwise; Va to Gas Cooler to Clean Coolant Drain; Ve from Ozone Generator to Vf; Vf from Ve through Gas Cooler to Gas Inlet; open the Gas Inlet; open the Gray Water Drain. Upon completion, close the Gas Inlet and the Gray Water Drain.

C.5: Repeat the Rinse Cycle (B.3 & B.4) multiple times.

Drying of the contents within the capsule is also done automatically under the control of an embedded microprocessor. This involves operating the peristaltic pump while dry sterile gas is being injected into and exhausted from the Wash Chamber; maintaining a positive pressure relative to atmospheric, to assure sterility of the contents; and tilting the Wash Chamber Capsule back to horizontal; Va to Gas Cooler to Clean Coolant Drain; Ve from Ozone Generator to Hot Catalytic Deozonator; Vf from Hot Catalytic Deozonator (or from the Inert Gas source in an alternate embodiment), through Gas Cooler to Gas Inlet; open the Gas Inlet; open the Gas vent in a restricted manner so as to maintain a positive pressure; activate the Peristaltic Pump. Upon completion of the Drying Cycle, close the Gas Inlet and the Gas Vent; turn on the "Operation Completed" indicator lamp on the operator's control panel.

FIG. 18 is a perspective view of an embodiment of the endoscope cleaner/sterilizer apparatus.

Capsule 180 has inlet/outlet ports 183A. Peristaltic zone 194 is, in the preferred embodiment, a clear flexible material. The endoscope, not shown, is inserted into capsule 180 via port 193 which is resealable.

The cleaner/sterilizer 181 has tilt tray 182 built into the top of the mechanism. Tilt tray 182 accepts capsule 180 and communicates with the capsule's inlet/outlet ports 183A via inlet/outlet ports 183B.

Although this embodiment utilizes an exposed tilt tray, those of ordinary skill in the art readily recognize that other arrangements are possible. One Such arrangement utilizes a circular slot opening in the housing in which the capsule is inserted; upon complete insertion, the inlets and outlets are automatically coupled. Upon removal, the inlets and outlets automatically seal.

Once the capsule is placed in tilt tray 182, pump mechanism 184 is hinged 184A down onto the peristaltic zone 194, as shown by arrow 187, to engage rollers 185 and 185A therewith. The cleaner/sterilizer 181 uses it's embedded microprocessor 197 to control the movement of roller 185 and tilt tray 182.

Fluid and gas inlets and outlets and other connections are made with the cleaner/sterilizer 181 via connections 191, 192, and others not shown.

When the capsule is properly positioned, the operator engages the "ON" button 188 and then selects which sequence (e.g. A, B, C) 189 that is desired. The microprocessor 197 within the cleaner/sterilizer 181 then controls the operation and communicates with the operator via status lamps 190.

Once the cleaning is complete, capsule 180 is removed from the cleaner/sterilizer 181. Upon removal, inlet/outlet valves 183A automatically seal creating a hermetically sealed environment within capsule 180 so that the now cleaned and sterilized endoscope can be stored within capsule 180.

In one embodiment of the invention, the operator enters in an identifying serial number for the endoscope. This serial number is used by the embedded microprocessor 197 to monitor the life of the endoscope so that proper refurbishing can be done at the proper time. In this embodiment, an LCD display is used to advise the operator when it is time to return the endoscope to the manufacturer for its periodic maintenance check.

In one embodiment of the capsule, an indicator 195, being an LCD alpha/numeric display, is used to indicate the status of the contents of the capsule (e.g. "empty", "sterile", "cleaned", "unsterile" "process aborted", "unsterile- refurbish"). This indicator 195 is set by the agitator's embedded microprocessor and is used to monitor the status of the cleaning/sterilizing process and to assure that the endoscopes are refurbished at the proper times.

An on-board processor 196 in the capsule 180 utilizes signals from the agitator's microprocessor 197 together with a sensor's signal 196A, indicative of the entry port's status, in establishing the capsule's 195 content.

In another embodiment, a pressure sensor communicating with the interior of the capsule monitors the internal pressure and displays the information via pressure indicator 198 to assure the operator that the sterilized instrument is sterile as long as the pressure Within the capsule is greater than the ambient pressure. This further safety feature assures that a sterilized endoscope which has been stored, will be sterile when it is used and that no leakage has occurred within the capsule during the storage period.

In the preferred embodiment for the endoscope cleaning/sterilizing mechanism, all indicators are pneumatic-mechanical and are not electronic to assure proper functioning and the only microprocessor in the system is the embedded microprocessor 197.

It is clear from the foregoing that the present invention provides for new and improved cleaning and sterilization mechanism, and involves the use of numerous inventions.

What is claimed is:

1. A tubing cleaning mechanism comprising:
   a) a capsule for holding said tubing, said capsule having,
      1) a liquid inlet port and a liquid outlet port, said liquid inlet port and said liquid outlet port automatically sealing upon disengagement,
      2) a resealable entry port for depositing said tubing in said capsule, and,
      3) a flexible peristaltic zone being deformable under pressure, said peristaltic zone forming a wall portion of said capsule;
   b) a diaphragm placed in said capsule and encircling said tubing, said diaphragm forming a partial seal in said capsule and dividing said capsule into a first section and a second section;
   c) a liquid source providing as chosen liquid; and,
   d) an agitator having,
      1) a tray for accepting and holding said capsule,
      2) pressure means for applying pressure to said flexible peristaltic zone,
      3) motor means for moving said pressure means over a portion of said peristaltic zone proximate to said diaphragm,
      4) communication means for communicating said liquid from said liquid source to said capsule via the liquid inlet port, and,
      5) control means for,
         A) causing said communication means to communicate said liquid to said capsule, B) directing said motor means to cycle said pressure means over said peristaltic zone for a selected period of time, and, C) opening the liquid outlet port to drain liquid from said capsule.

2. The cleaning mechanism according to claim 1 further including:
   a) a detergent reservoir containing detergent therein;
   b) mixing means for mixing liquid from said liquid source and detergent from said detergent reservoir; and,
   c) means for selectively communicating a mixture of liquid and detergent from said mixing means to said capsule via said liquid inlet port.

3. The cleaning mechanism according to claim 2 wherein said capsule further includes a vapor inlet port and a vapor outlet port, and further including a sterile gas source providing a sterile gas, further including means for selectively communicating said sterile gas to said capsule via said vapor inlet port.

4. The cleaning mechanism according to claim 3 further including:
   a) an ozone generator means for generating ozone gas; and,
   b) means for selectively mixing ozone frog said ozone generator means with said sterile gas prior to communicating said sterile gas to said capsule.

5. The cleaning mechanism according to claim 3 wherein said control means includes drying means for selectively opening the vapor outlet port of said capsule.

6. The cleaning mechanism according to claim 2 wherein said agitator includes:
   a) an operator interface for receipt of identifier data which identifies said endoscope; and,
   b) a memory unit for storage of said identifier data.

7. The cleaning mechanism according to claim 6 wherein said agitator further includes a display means for displaying alphanumeric information to an operator, and wherein said control means includes means for:
   a) maintaining a running count of the number of times said endoscope in said capsule has been placed on said tray; and,
   b) communicating said identifier data from said memory unit and said running count to an operator via said display means.

8. The cleaning mechanism according to claim 7 wherein said control means has means for refusing operation when said running count reaches a preselected value.

9. The cleaning mechanism according to claim 7 wherein said capsule further includes:
   a) a display means for communicating alphanumeric characters to the operator; and,
   b) a processing means for establishing status information on said display means in response to signals from the control means of said agitator.

10. The cleaning mechanism according to claim 9 further including sensor means generating a signal indicative of the open/closed state of said resealable entry port of said capsule and wherein said processing means in said capsule is responsive to the signal from said sensor means in generating said status information.

11. An endoscope cleaning apparatus comprising:
   a) a capsule for holding said endoscope, said capsule having,
      1) a resealable entry port for depositing said endoscope into said capsule, and,
      2) a flexible peristaltic zone being deformable under pressure;
   b) a diaphragm encircling said endoscope within said capsule and providing a partial Seal within said capsule;
   c) a liquid contained within said capsule; and,
   d) an agitator having,
      1) a tray for accepting said capsule,
      2) pressure means for applying pressure to said flexible peristaltic zone of said capsule, and,
      3) motor means for oscillating said pressure means over a section of said flexible peristaltic zone.

12. The endoscope cleaning apparatus according to claim 11 wherein said capsule further includes at least one inlet port and at least one outlet port, said inlet port and said outlet port automatically sealing upon disconnection.

13. The endoscope cleaning apparatus according to claim 12 wherein said agitator includes:
   a) means for generating an ozone gas; and,
   b) means for selectively communicating said ozone gas into said capsule via said inlet port.

14. The endoscope cleaning apparatus according to claim 13 wherein said liquid is inserted into said capsule via said inlet port and further including means for mixing said ozone gas in said liquid.

15. The endoscope cleaning apparatus according to claim 13 wherein said agitator includes:
   a) means for purifying water from a water source;
   b) a detergent reservoir means for holding detergent; and,
   c) means for communicating water from said means for purifying and detergent from said detergent reservoir means to said capsule.

16. The endoscope cleaning apparatus according to claim 12 wherein said agitator includes:
   a) an operator interface for receipt of identifier data which identifies said endoscope; and,
   b) a memory unit for storage of said identifier data.

17. The endoscope cleaning apparatus according to claim 16 wherein said agitator further includes a display means for displaying alphanumeric information to an operator, and wherein said control means includes means for:
   a) maintaining a running count of the number of times said endoscope in said capsule has been placed on said tray; and,
   b) communicating said identifier data from said memory unit and said running count to an operator via said display means.

18. The endoscope cleaning apparatus according to claim 17 wherein said control means has means for refusing operation when said running count reaches a preselected value.

19. The endoscope cleaning apparatus according to claim 17 wherein said capsule further includes:
   a) a display means for communicating alphanumeric characters to the operator; and,
   b) a processing means for establishing status information on said display means in response to signals from the control means of said agitator.

20. The endoscope cleaning apparatus according to claim 19 further including sensor means Generating a signal indicative of the open/closed state of said resealable entry port of said capsule and wherein said processing means in said capsule is responsive to the signal from said sensor means in generating said status information.

21. A tubing sterilizing mechanism comprising:

a) a capsule for holding said tubing, said capsule having,
 1) a liquid inlet port and a liquid outlet port, said liquid inlet port and said liquid outlet port automatically sealing upon disengagement,
 2) a resealable entry port for depositing said tubing in said capsule,
 3) a vapor inlet port and a vapor outlet port, said vapor inlet port and said vapor outlet port automatically sealing upon disengagement,
 4) a flexible peristaltic zone being deformable under pressure, said peristaltic zone forming a wall portion of said capsule;
b) a diaphragm placed in said capsule and encircling said tubing, said diaphragm forming a partial seal in said capsule and dividing said capsule into a first section and a second section;
c) a detergent reservoir containing detergent therein;
d) a liquid source providing a chosen liquid;
e) mixing means for mixing liquid from said liquid source and detergent from said detergent reservoir;
f) a sterile gas source providing a sterile gas;
g) an ozone generator means for generating ozone gas; and,
h) an agitator having,
 1) a tray for accepting and holding said capsule, said tray having four valves for engaging said liquid inlet port, the liquid outlet port, the vapor inlet port, and the vapor outlet port,
 2) pressure means for applying pressure to said flexible peristaltic zone,
 3) motor means for moving said pressure means over a portion of said peristaltic zone proximate to said diaphragm,
 4) communication means for communicating said liquid from said liquid source to said capsule via the liquid inlet port, and,
 5) control means for,
  A) communicating a mixture of liquid and detergent from said mixing means to said capsule via said liquid inlet port;
  B) causing said communication means to communicate said liquid to said capsule,
  C) directing said motor means to cycle said pressure means over said peristaltic zone for a selected period of time, and,
  D) opening the liquid outlet port to drain liquid from said capsule
  E) mixing ozone from said ozone generator means with said sterile gas,
  F) communicating sterile gas and ozone to said capsule via said vapor inlet port; and,
  G) exhausting excess sterile gas from said capsule via said vapor outlet port.

22. The tubing sterilizing mechanism according to claim 21 wherein said agitator includes:

a) an operator interface for receipt of identifier data which identifies said endoscope; and,
b) a memory unit for storage of said identifier data.

23. The tubing sterilizing mechanism according to claim 22 wherein said agitator further includes a display means for displaying alphanumeric information to an operator, and wherein said control means includes means for:
a) maintaining a running count of the number of times said endoscope in said capsule has been placed on said tray; and,
b) communicating said identifier data from said memory unit and said running count to an operator via said display means.

24. The tubing sterilizing mechanism according to claim 23 wherein said control means has means for refusing operation when said running count reaches a preselected value.

25. The tubing sterilizing mechanism according to claim 23 wherein said capsule further includes:
a) a display means for communicating alphanumeric characters to the operator; and,
b) a processing means for establishing status information on said display means in response to signals from the control means of said agitator.

26. The tubing sterilizing mechanism according to claim 25 further including sensor means generating a signal indicative of the open/closed state of said resealable entry port of said capsule and wherein said processing means in said capsule is responsive to the signal from said sensor means in generating said status information.

27. The tubing sterilizing mechanism according to claim 26 further including pressure sensor means generating a pressure signal indicative of the pressure difference between an interior portion of said capsule and an ambient pressure, and wherein said processing means is responsive to said pressure signal in generating said status information.

28. A device for holding an endoscope during sterilization, said device comprising:
a capsule having a first end, said first end including a resealable entry port for depositing said endoscope into said capsule; a middle portion including a flexible peristaltic zone being deformable under pressure; and a second end including 1) a processing means for establishing a status condition within said capsule, and 2) a display means for communicating alphanumeric characters indicating said status condition of said capsule to an operator.

29. The capsule according to claim 28 wherein said first end further includes sensor means generating a status signal indicative of an open/closed state of said resealable entry port of said capsule and wherein said processing means is responsive to the status signal from said sensor means in generating said status condition.

* * * * *